US012661148B2

(12) United States Patent
Koarashi

(10) Patent No.: US 12,661,148 B2
(45) Date of Patent: Jun. 23, 2026

(54) INSERTING MEMBER LEAD-OUT DEVICE

(71) Applicant: HI-LEX CORPORATION, Hyogo (JP)

(72) Inventor: Shinsaku Koarashi, Hyogo (JP)

(73) Assignee: HI-LEX CORPORATION, Hyogo (JP)

( * ) Notice: Subject to any disclaimer, the term of this patent is extended or adjusted under 35 U.S.C. 154(b) by 391 days.

(21) Appl. No.: 18/580,843

(22) PCT Filed: Mar. 31, 2022

(86) PCT No.: PCT/JP2022/016428
§ 371 (c)(1),
(2) Date: Aug. 1, 2024

(87) PCT Pub. No.: WO2023/002721
PCT Pub. Date: Jan. 26, 2023

(65) Prior Publication Data
US 2025/0331891 A1      Oct. 30, 2025

(30) Foreign Application Priority Data

Jul. 19, 2021    (JP) ................................. 2021-118785

(51) Int. Cl.
*A61B 17/34* (2006.01)
*A61B 17/00* (2006.01)

(52) U.S. Cl.
CPC ..................... *A61B 17/3468* (2013.01); *A61B 2017/00477* (2013.01); *A61B 2017/3492* (2013.01)

(58) Field of Classification Search
None
See application file for complete search history.

(56) References Cited

U.S. PATENT DOCUMENTS

2004/0176781 A1* 9/2004 Lindstrom ......... A61B 17/3468
606/129
2005/0107861 A1* 5/2005 Harris .................. A61N 1/0551
607/116
(Continued)

FOREIGN PATENT DOCUMENTS

JP        S62202847 U      12/1987
JP        2005342508 A     12/2005
(Continued)

OTHER PUBLICATIONS

International Search Report from corresponding PCT Application No. PCT/JP2022/016428, Jun. 21, 2022.
(Continued)

*Primary Examiner* — Shaun L David
(74) *Attorney, Agent, or Firm* — Workman Nydegger

(57) ABSTRACT

The present invention is an inserting member lead-out device comprising a main body, a perforating member for forming a perforation hole being perforated in the wall-like tissues in a first direction, and a connector configured to connect the perforating member and an inserting member, wherein the perforating member has a tip portion and a perforating shaft portion, wherein the maximum dimension of the perforating shaft portion is smaller than the outer diameter of the inserting member, wherein the main body has a lead-out hole extending along the first direction, wherein the perforating member is configured to be guided in the first direction and a second direction coaxially to the axial center of the lead-out hole, and wherein the lead-out hole has a size allowing the connector and the inserting member to be inserted through the lead-out hole.

6 Claims, 11 Drawing Sheets

(56) References Cited

U.S. PATENT DOCUMENTS

| | | | | |
|---|---|---|---|---|
| 2006/0235431 | A1* | 10/2006 | Goode | A61B 17/3468 606/108 |
| 2008/0071341 | A1* | 3/2008 | Goode | A61B 17/32002 607/122 |
| 2010/0030227 | A1* | 2/2010 | Kast | A61N 1/0553 606/129 |
| 2010/0057176 | A1* | 3/2010 | Barker | A61N 1/0551 607/117 |
| 2012/0323252 | A1* | 12/2012 | Booker | A61N 1/056 606/129 |
| 2013/0158564 | A1* | 6/2013 | Harris | A61B 17/34 606/129 |
| 2014/0039586 | A1* | 2/2014 | Barker | A61B 17/3468 607/116 |
| 2014/0276927 | A1* | 9/2014 | Barker | A61M 25/0668 606/129 |
| 2015/0073431 | A1* | 3/2015 | Barker | A61N 1/0551 606/129 |
| 2021/0402150 | A1 | 12/2021 | Koarashi | |
| 2022/0211978 | A1 | 7/2022 | Koarashi | |

FOREIGN PATENT DOCUMENTS

| | | |
|---|---|---|
| JP | 2010069224 A | 4/2010 |
| JP | 2014200299 A | 10/2014 |
| JP | 2020081537 A | 6/2020 |
| WO | 2020230681 A1 | 11/2020 |

OTHER PUBLICATIONS

Indian Office Action from Corresponding Indian Patent Application No. IN202317083722, Mar. 9, 2026.

* cited by examiner

INSERTING MEMBER LEAD-OUT DEVICE

TECHNICAL FIELD

The present invention relates to an inserting member lead-out device.

BACKGROUND ART

A linear inserting member can be passed through the wall-like tissues of the living body from one side of the wall-like tissues to the other side of the wall-like tissues when treating the living body, including the human body, and the like. For example, Patent document 1 discloses a skin button for arranging a driveline. To supply electric power to a ventricular assist device (VAD) implanted in the human body, the driveline is arranged by the skin button at a predetermined angle with respect to the wall-like tissues of the human body in a state where the driveline passes through the wall-like tissues of the human body, such as the skin, the fascia, the muscular layer, the peritoneum, and the like. The skin button has a communicating portion through which the driveline is inserted and a flange portion provided in a flange shape around the communicating portion. The skin button is fixed to the skin of the human body with the flange portion being arranged between the epidermis and the dermis of the skin.

When pulling out the above-described driveline from the abdominal cavity to the outside of the body, a tunneler to form an insertion hole through which the driveline is to be inserted in the wall-like tissues of the human body can be used. In this case, after the driveline is inserted through the insertion hole being formed with the tunneler in the human body, and then the driveline is inserted through the skin button and the skin button is arranged in the skin of the human body. Therefore, the skin button can be fixed to the skin of the human body.

PRIOR ART DOCUMENT

Patent Document 1: JP 2020-81537 A

SUMMARY OF THE INVENTION

Problem to be Solved by the Invention

However, when carrying out an operation to form the insertion hole with the tunneler, deviation can occur in the position and angle at which the insertion hole is formed relative to the ideal position and angle which is intended to be formed originally. In this way, when the driveline is inserted through the insertion hole having deviation in the position and angle, the position and angle of the driveline arranged in the insertion hole are deviated. Therefore, when the driveline is inserted through the skin button and the skin button is fixed to the skin, the skin button can lift or sink relative to the skin, possibly inhibiting the promotion of initial treatment of tissues due to tensile load or compressive load on the skin tissues.

Then, an object of the present invention is to provide an inserting member lead-out device which can accurately and easily lead out, to the outside the body, an inserting member to be inserted into the wall-like tissues of the living body.

Means to Solve the Problem

An inserting member lead-out device of the present invention is an inserting member lead-out device for inserting a linear inserting member through wall-like tissues of the living body, the inserting member lead-out device comprising: a main body being arrangeable on one side of the wall-like tissues in a wall-thickness direction of the wall-like tissues; a perforating member for forming a perforation hole being perforated in the wall-like tissues in a first direction from the one side toward an other side, wherein the perforating member is movable relative to the main body; and a connector configured to connect the perforating member and the inserting member, wherein the connector comprises a first connecting portion being connectable to the perforating member at one end side of the connector and a second connecting portion being connectable to the inserting member at an other end side of the connector, wherein the perforating member has a tip portion, and a perforating shaft portion to be a part inserted into the wall-like tissues, wherein the perforating shaft portion is adjacent to the tip portion in a length direction of the perforating member, wherein a maximum dimension of the perforating shaft portion in a radial direction of the inserting member is smaller than an outer diameter of the inserting member, wherein the main body has a lead-out hole having an inner space extending along the first direction, wherein the perforating member is configured to be guided in the first direction and in a second direction opposite to the first direction in an interior of the lead-out hole coaxially to an axial center of the lead-out hole, and wherein the lead-out hole has a size allowing the connector and the inserting member to be inserted through the lead-out hole when the perforating member is moved in the second direction in a state in which the perforating member is connected to the connector with the connector being connected to the inserting member at the other side of the wall-like tissues.

Effects of the Invention

The inserting member lead-out device of the present invention can accurately and easily lead out, to the outside the body, an inserting member to be inserted into the wall-like tissues of the living body.

EMBODIMENT FOR CARRYING OUT THE INVENTION

Below, an inserting member lead-out device of one embodiment of the present invention will be described with reference to the drawings. Besides, in the present specification, the expression "perpendicular to A" and that similar thereto are to refer to not only a direction being completely perpendicular to A, but to refer to include being substantially perpendicular to A. Moreover, in the present specification, the expression "parallel to B" and that similar thereto are to refer to not only a direction being completely parallel to B, but to refer to include being substantially parallel to B. Furthermore, in the present specification, the expression "a C-letter shape" and that similar thereto are to refer to not only a complete C-letter shape, but to refer to include a shape suggesting a C-letter shape in appearance (a substantially C-letter shape).

An inserting member lead-out device 1 of the present embodiment is used for inserting a linear inserting member I (see FIG. 1) through wall-like tissues T of the living body (see FIGS. 9 to 13). While details will be described below, as shown in FIGS. 9 to 13, when a perforation hole H1 (see FIG. 4) is formed from one side Ta to the other side Tb in a wall-thickness direction TD of the wall-like tissues T of the living body and then the inserting member I moves from the other side Tb to the one side Ta of the wall-like tissues T, the perforation hole H1 is widened by a connector 4 to be described below and an insertion hole H2 (see FIGS. 1 and 13) larger than the perforation hole H1 is formed. In this way, the inserting member I is inserted through the insertion hole H2 of the wall-like tissues T and the inserting member I is led out from the wall-like tissues T.

In the present specification, the term "the living body" refers to the human body, and the body of an animal other than a human. The term "wall-like tissues" refers to arbitrary tissues of the living body, such as a wall, a membrane, and the like, which can be perforated with a perforating member 3 to be described below (see FIG. 2) and have a perforatable predetermined thickness Specifically, the wall-like tissues refer to various tissues in the living body, such as the skin (the epidermis, the dermis, the subcutaneous tissues), the muscular layer, the tissues constituting various organs, and the like, and a layer in which these are combined. In the present embodiment, the wall-like tissues T through which the inserting member I is to be inserted are tissues including the skin and the muscular layer. Moreover, in the present embodiment, the one side Ta of the wall-like tissues Tis a side at the outside of the body, while the other side Tb of the wall-like tissues T is a side at the inside of the body. It should be noted that one side and the other side of the wall-like tissues can be either side of the wall-like tissues and can be changed as needed according to the use of the inserting member lead-out device.

Figure 1:
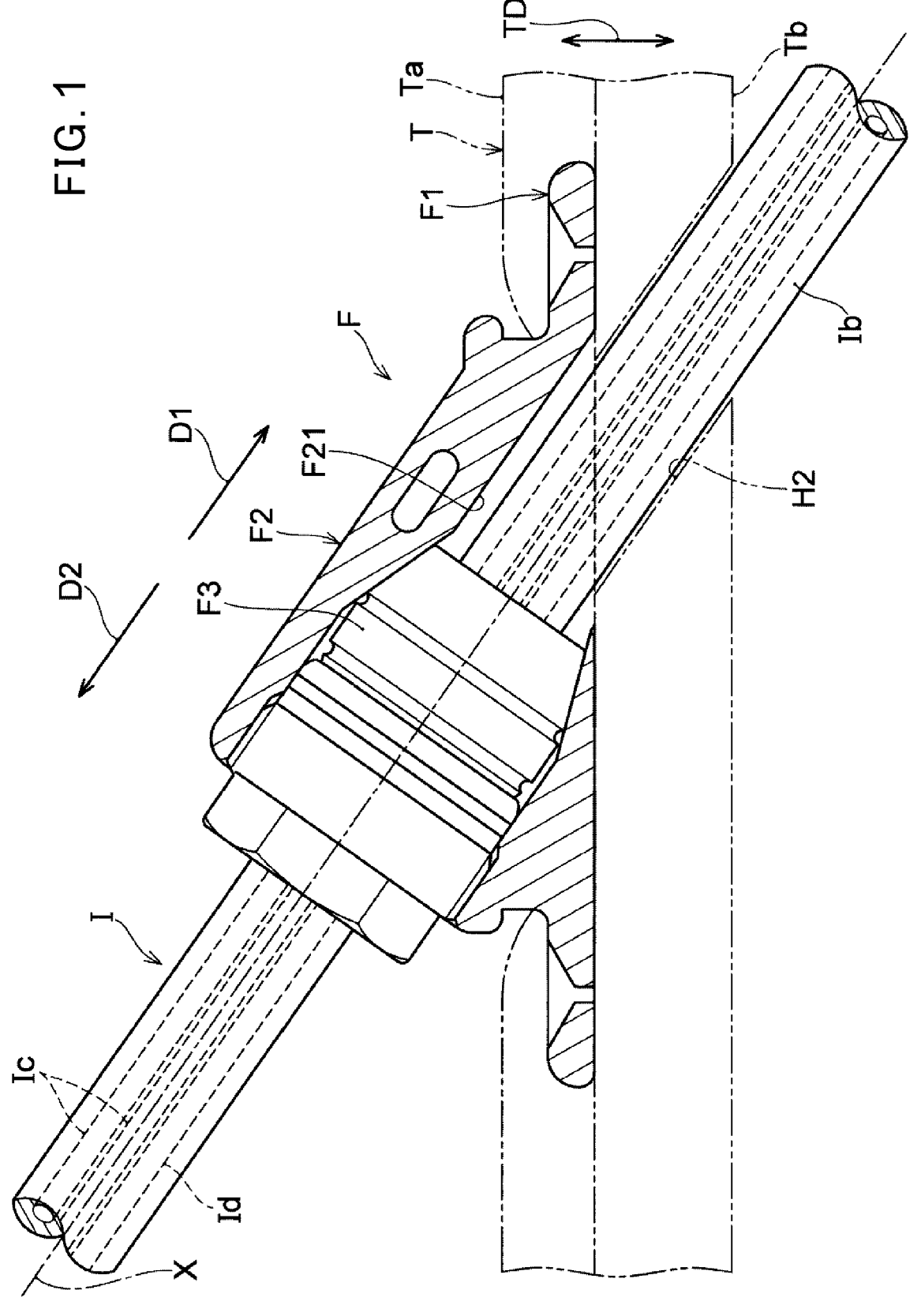
FIG. 1 is a view showing a state in which an inserting member inserted through an insertion hole formed in the wall-like tissues is fixed to the wall-like tissues with a fixing device.

In the present embodiment, the inserting member lead-out device 1 is used to lead out, to the outside the body, the inserting member I to be inserted through a fixing device F (see FIG. 1) to be fixed to the wall-like tissues T. More specifically, the inserting member lead-out device 1 is used to insert a driveline (the inserting member I), which is used for a medical device (for example, an artificial organ such as a ventricular assist device (VAD), an artificial lung, and the like) implanted into the human body, through the skin, the muscular layer, which are the wall-like tissues T of the abdomen and to lead out the driveline from the inside to the outside of the human body. As shown in FIG. 1, the driveline led out to the outside of the body is fixed at a predetermined position of the abdomen via the fixing device F.

The inserting member I has a predetermined length and is a member to be inserted through the wall-like tissues T of the living body. The term "linear" in the linear inserting member I means that the inserting member I extends for a predetermined length regardless of whether the inserting member I is hollow or solid. In the present embodiment, the inserting member I is an elongated member for medical use to be arranged with the inserting member I being passed through the wall-like tissues T of the living body from the one side Ta to the other side Tb of the wall-like tissues T. More specifically, the inserting member I is a driveline for an artificial organ (a ventricular assist device). One end of the inserting member I is coupled to an artificial organ (not shown) arranged at a predetermined position inside of the body, while the other end of the inserting member I is coupled to a device (a power supply and the like) arranged outside of the body. As described below, the inserting member I is inserted through the wall-like tissues T of the living body before it is coupled to the device arranged outside of the body and led out from the inside to the outside of the body.

Figure 2:
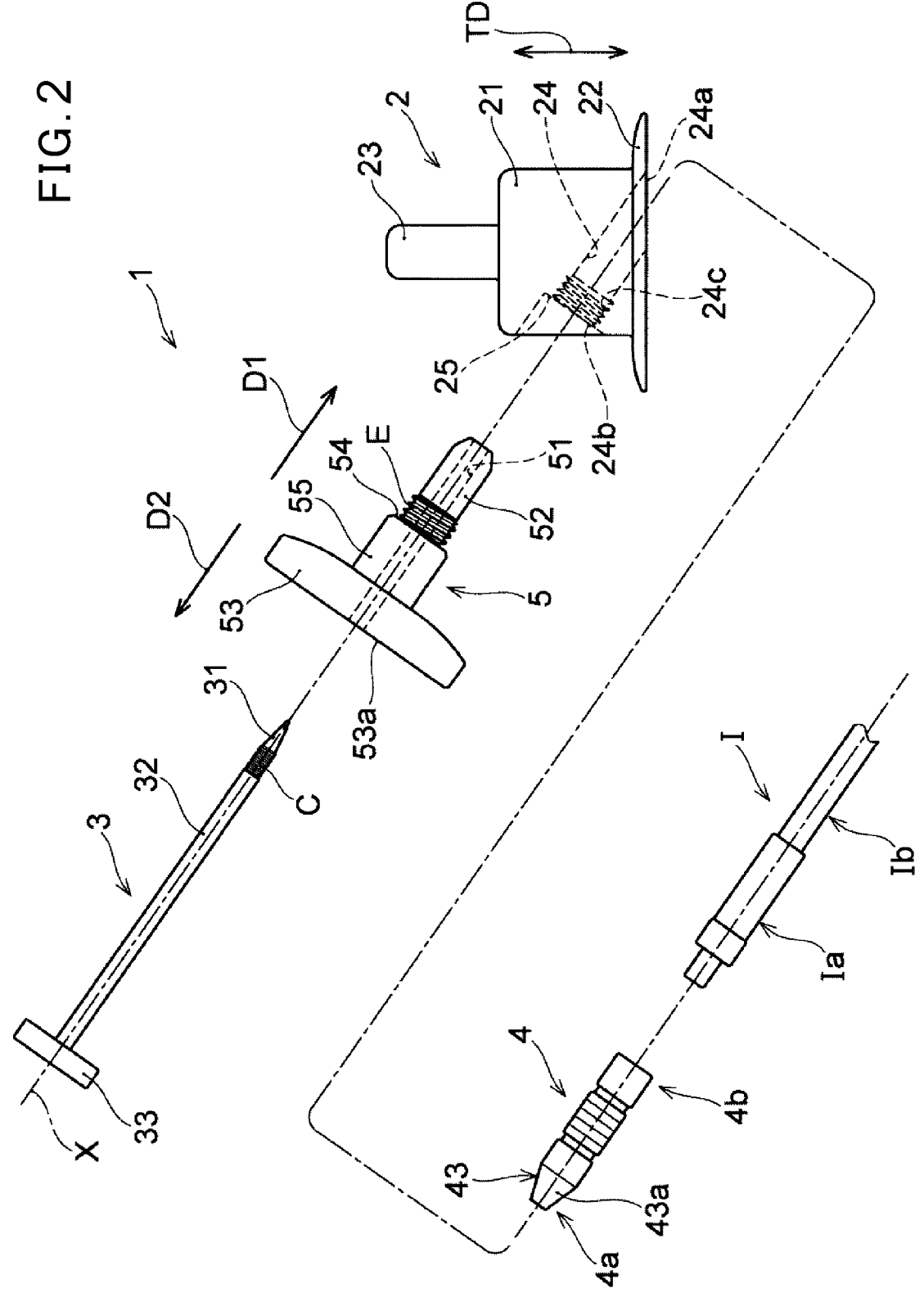
FIG. 2 is an exploded view of an inserting member lead-out device of one embodiment of the present invention.
Figure 4:
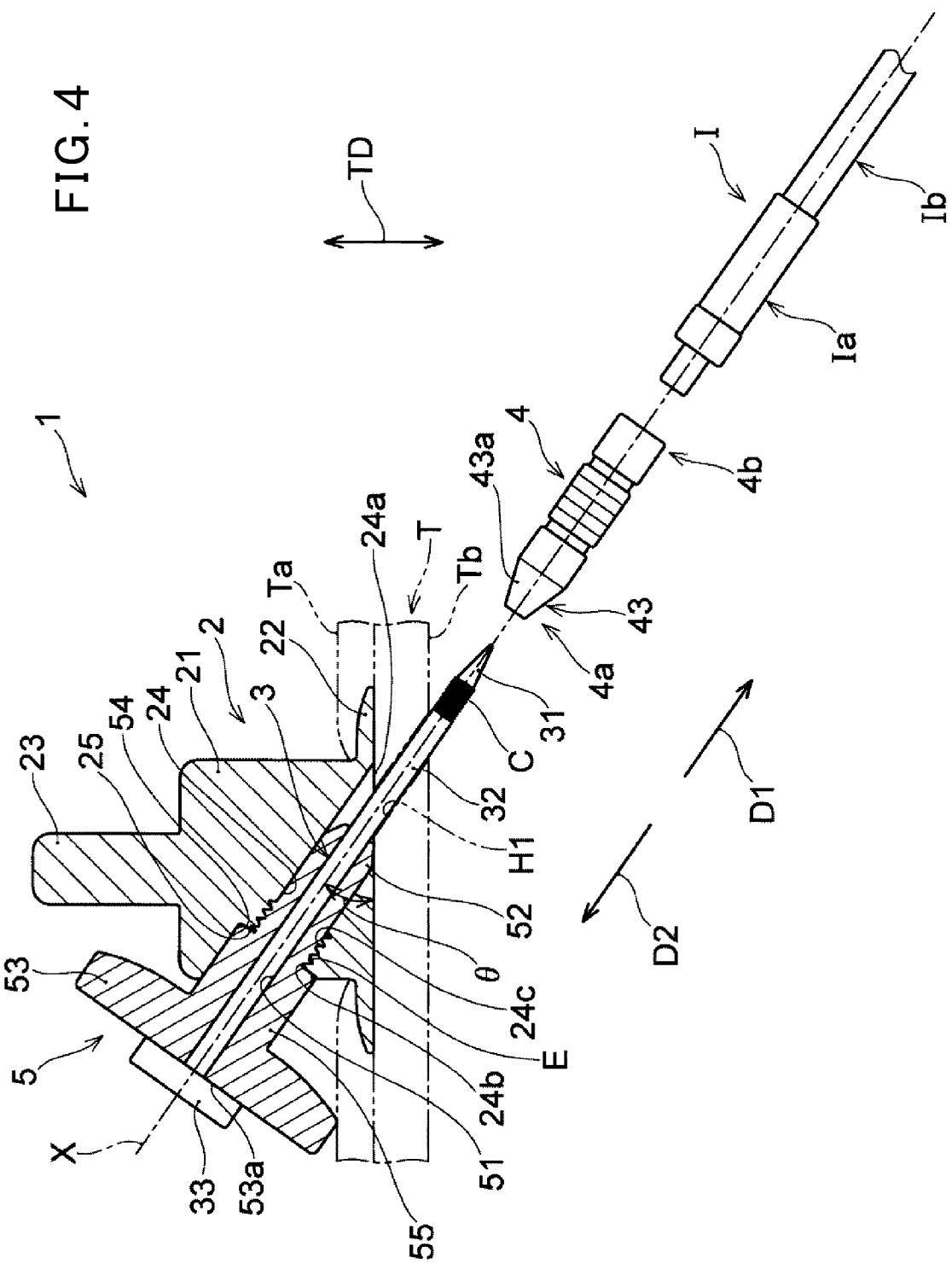
FIG. 4 is a partial cross-sectional view showing a state in which the perforating member moves in a first direction from the state shown in FIG. 3 and the perforating member perforates the wall-like tissues.

As shown in FIGS. 2 and 4, the inserting member I has a coupling portion Ia provided at the other end of the inserting member I to couple to a device arranged outside of the body, and an inserting member main body Ib. The coupling portion Ia can be configured to be a substantially cylindrical plug (a male plug) to be connected to a power supply connecting portion (a female plug) of a device arranged outside of the body, such as a power supply, for example. However, the shape and structure of the coupling portion Ia are not limited. In the present embodiment, as shown in FIGS. 2 and 4, the outer diameter of the coupling portion Ia is configured to be larger than the outer diameter of the inserting member main body I*b*. However, the outer diameter of the coupling portion I*a* may be smaller than or may be the same as the outer diameter of the inserting member main body I*b*. In the present embodiment, the inserting member main body I*b* has a predetermined flexibility and rigidity. The inserting member main body I*b* has a predetermined elasticity that tends to cause the inserting member main body I*b* to restore and return to the original shape thereof when the inserting member main body I*b* is subjected to bending deformation.

The internal structure of the inserting member I is not limited, but, in the present embodiment, as shown in FIG. 1, the inserting member I has a cooling water circulation path I*c* to circulate cooling water between an artificial organ inside of the body and a pressure pump outside of the body, and a power cable I*d* to couple the artificial organ inside of the body and a power supply outside of the body. It should be noted that the inserting member I may be configured to have only a power cable, may be configured to have only a cooling water circulation path, may be configured to have a member having another function, and the like, or may be configured as a hollow member not having any member in the interior thereof. When the inserting member I is used as a hollow member to communicate between the inside and the outside of the body, the inserting member I may be used to deliver a drug for treatment from the outside of the body to a site to be treated inside of the body.

When the inserting member I is inserted through the wall-like tissues T by the inserting member lead-out device 1, for example, as shown in FIG. 1, the inserting member I is inserted through the fixing device F and the fixing device F is fixed to the wall-like tissues T. In this way, the inserting member I is fixed at a predetermined position via the fixing device F with the inserting member I being inserted through the wall-like tissues T. In the present embodiment, the inserting member I is inserted through the wall-like tissues T by the inserting member lead-out device 1 (see FIG. 13), then the inserting member lead-out device 1 is removed, and the fixing device F, which is a member different from the inserting member lead-out device 1, is fixed to the wall-like tissues T (see FIGS. 1 and 14). However, as long as the inserting member lead-out device 1 comprises functions necessary as the fixing device F, the inserting member lead-out device 1 may be used as the fixing device as it is without removing the inserting member lead-out device 1 from the wall-like tissues T.

As the fixing device F, a known fixing device known as a so-called skin button may be used, so that detailed explanations thereof will be omitted. As one example, as shown in FIG. 1, the fixing device F has a fixing portion F1 to be fixed to the wall-like tissues T, a communicating portion F2 having a communicating path F21 through which the inserting member I is inserted, and a chuck member F3 to liquid-tightly fix the inserting member I. A surface treatment is preferably applied to at least a part of the fixing device F to promote anchoring of a part of the wall-like tissues T (the skin). Moreover, as for the material of the fixing device F, the fixing device F is preferably formed of a material having biocompatibility. Examples of the material having biocompatibility include, for example, titanium, a titanium alloy, and the like for a metal material, and a high-strength polytetrafluoroethylene (PTFE), polyetheretherketone (PEEK), and the like by compression molding for a resin material. The material to be used for the fixing device F is selected as needed according to the site at which the fixing device F is to be used, and the application of the fixing device F.

The wall-like tissues T (the skin tissues of the skin) incised are guided to the fixing portion F1 of the fixing device F and the wall-like tissues T are fixed to the fixing portion F1 of the fixing device F. In the present embodiment, the fixing portion F1 extends radially outward with respect to the communicating portion F2 at an end of the communicating portion F2 at a side of the wall-like tissues T. In the present embodiment, the fixing portion F1 is formed in the shape of a flange surrounding the communicating portion F2.

In the present embodiment, the communicating portion F2 communicates between the inside and the outside of the body. The communicating portion F2 is a portion through which the inserting member I is inserted and is configured in a substantially cylindrical shape. The chuck member F3 is a member to be arranged between the inner wall of the communicating path F21 of the communicating portion F2 and the outer surface of the inserting member I, and tightens and liquid-tightly holds the inserting member I. When the fixing device F with the inserting member I being inserted therethrough is fixed to the wall-like tissues T, cells propagate and the fixing device F is fixed to the wall-like tissues T.

Next, a configuration of the inserting member lead-out device 1 of the present embodiment will be explained.

Figure 3:
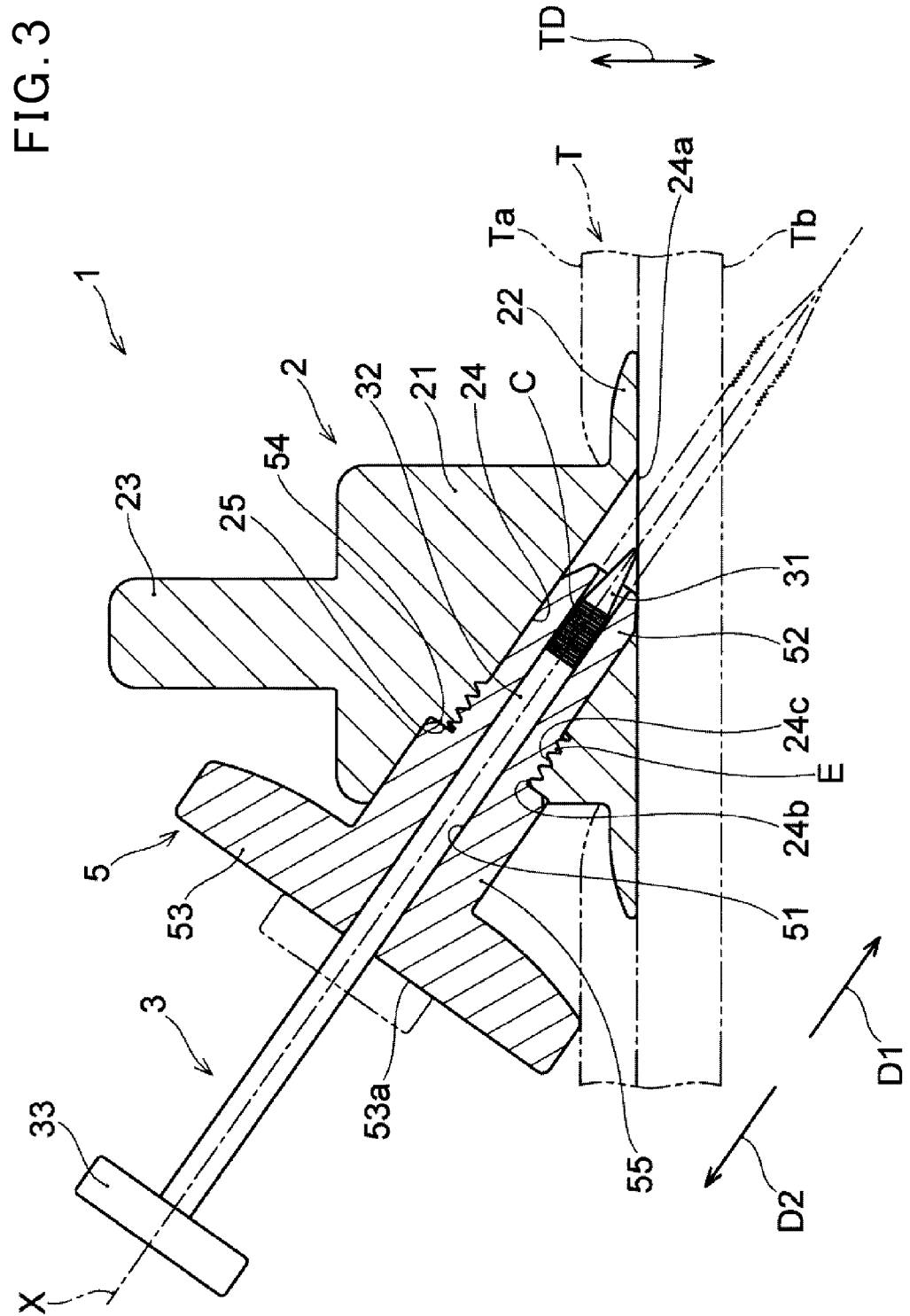
FIG. 3 is a partial cross-sectional view showing a state in which the inserting member lead-out device shown in FIG. 2 is assembled before a perforating member perforates the wall-like tissues.

As shown in FIGS. 2 to 4, the inserting member lead-out device 1 comprises a main body 2 being arrangeable on the one side T*a* of the wall-like tissues T in the wall-thickness direction TD of the wall-like tissues T, the perforating member 3 for forming a perforation hole H1 (FIG. 4) being perforated in the wall-like tissues T in a first direction D1 from the one side T*a* toward the other side T*b*, wherein the perforating member 3 is movable relative to the main body 2, and the connector 4 (see FIGS. 2 and 4) configured to connect the perforating member 3 and the inserting member I, wherein the connector 4 comprises a first connecting portion 41 (see FIGS. 7 and 8) being connectable to the perforating member 3 on one end 4*a* side of the connector 4 and a second connecting portion 42 (see FIGS. 7 and 8) being connectable to the inserting member I on the other end 4*b* side of the connector 4. Moreover, as shown in FIGS. 2 to 4, in the present embodiment, the inserting member lead-out device 1 further comprises a guide member 5.

In the present specification, the term "wall-thickness direction TD" refers to the thickness direction of the wall-like tissues T, or in other words, a direction connecting the surface at the one side T*a* of the wall-like tissues T and the surface at the other side T*b* of the wall-like tissues T. In the present embodiment, the wall-thickness direction TD is also a direction approaching or leaving the surface of (a direction perpendicular to the surface of) the wall-like tissues T (the surface at the outer side of the body or the surface at the inner side of the body). In the present specification, when explaining the respective components of the inserting member lead-out device 1, a direction parallel to the wall-thickness direction TD with the inserting member lead-out device 1 being arranged in the wall-like tissues T can similarly be called the wall-thickness direction TD. Moreover, the first direction D1 is a direction in which the perforating member 3 moves from the one side T*a* toward the other side T*b* when the perforating member 3 perforates the wall-like tissues T. The "first direction D1 from the one side T*a* toward the other side T*b*" may be inclined relative to the wall-thickness direction TD or may be parallel to the wall-thickness direction TD. In the present embodiment, an angle $\theta$ (see FIG. 4) formed by the first direction D1 (the axis X of the perforating member 3) and a surface of the wall-like tissues T, which opposes the main body 2 (a surface being tangent to a site at which the perforation hole H1 is formed in a case that the surface is curved) may be set to be, for example, 10° to 80°, preferably 20° to 70°, more preferably 30° to 60°. A second direction D2 is a direction opposite to the first direction D1 and refers to the moving direction in which the perforating member 3 moves when the perforating member 3 is withdrawn after the perforating member 3 perforates the wall-like tissues T. In the present specification, the direction including both the first direction D1 and the second direction D2 is referred to as the axis X direction (the axis X direction of the perforating member 3).

As shown in FIGS. 3 and 4, the main body 2 is a part to be arranged on the one side Ta of the wall-like tissues T in the wall-thickness direction TD. In the present embodiment, the main body 2 is fixed to the skin being the wall-like tissues T. The shape and structure of the main body 2 are not limited as long as the main body 2 may be arrangeable on the one side Ta of the wall-like tissues T in the wall-thickness direction TD and has a lead-out hole 24 to be described below. In the present embodiment, the main body 2 has a main body portion 21, a flange portion 22, and a grip portion 23.

The main body portion 21 is a part at which the lead-out hole 24 to be described below is provided and is a portion to be a base body occupying the majority of the main body 2. In the present embodiment, as shown in FIGS. 3 to 6, the main body portion 21 is formed in the shape of a column extending in the wall-thickness direction TD. The main body portion 21 has the lead-out hole 24 passing through the main body portion 21. In the present embodiment, the flange portion 22 extends outwardly perpendicularly to the wall-thickness direction TD from the outer periphery of one end of the main body portion 21 in the wall-thickness direction TD (at a side of the wall-like tissues T) (see FIGS. 5 and 6). The flange portion 22 is preferably shaped and sized in correspondence with the fixing portion F1 of the fixing device F. The grip portion 23 is a part to be gripped by the operator when using the inserting member lead-out device 1, such as when moving the main body 2, when perforating with the perforating member 3, when leading-out the inserting member I, and the like.

It should be noted that a method of fixing the main body 2 to the wall-like tissues T is not limited. In the present embodiment, the skin (the wall-like tissues T) of a size corresponding to the size of the main body portion 21 is (are) excised, and the skin of the portion corresponding to the flange portion 22 is incised so that the flange portion 22 slips beneath the skin. In this way, as shown in FIG. 3, the main body 2 is fixed to the wall-like tissues T with the flange portion 22 slipping beneath the skin and the main body portion 21 being exposed from the skin. In the present embodiment, a part of the main body 2 to be arranged in the wall-like tissues T has a shape corresponding to the above-described fixing device F, and the fixing device F can be fixed to the wall-like tissues T in the same state (position and orientation, for example) as the main body 2 after the main body 2 is removed from the wall-like tissues T. In this case, an operation of fixing the fixing apparatus F to the wall-like tissues T can be carried out easily. Moreover, in a case that the communicating path F21 of the fixing apparatus F and the lead-out hole 24 of the main body 2 extend with the same size, the same position, and the same angle, as described below, the fixing device F is less likely to be subjected to a force from the inserting member I in a direction to displace the fixing device F relative to the desired position of the fixing device F when the inserting member I is inserted through the communicating path F21 of the fixing apparatus F. In this case, as described below, lifting or sinking of the fixing device F relative to the wall-like tissues T can be suppressed.

As long as it is unlikely that the main body 2 is displaced in position relative to the wall-like tissues T, a different method of fixing such as a medical tape, and the like, for example, may also be used as a method of fixing the main body 2 to the wall-like tissues T. Moreover, the main body 2 may be fixed to the wall-like tissues T temporarily, such as only during surgery, or the main body 2 may be fixed to the wall-like tissues T over a long period of time as needed for patient treatment or permanently. Furthermore, the material forming the main body 2 is not limited, but, for the material forming the main body 2, a metal or a resin having biocompatibility may be used, for example.

As described above, as shown in FIGS. 2 to 4, the main body 2 has the lead-out hole 24 having the inner space extending along the first direction D1. Moreover, while details will be described below, the lead-out hole 24 has a size allowing the connector 4 and the inserting member I to be inserted through the lead-out hole 24 when the perforating member 3 is moved in the second direction D2 in a state in which the perforating member 3 is connected to the connector 4 with the connector 4 being connected to the inserting member I at the other side Tb of the wall-like tissues T (see FIGS. 12 and 13). Moreover, in the present embodiment, as shown in FIGS. 3 and 4, the lead-out hole 24 is configured such that the perforating member 3 passes through the lead-out hole 24 when the perforating member 3 perforates the wall-like tissues T. Furthermore, in the present embodiment, at least a part of the guide member 5 is inserted into the lead-out hole 24.

The lead-out hole 24 extends along the first direction D1 (the axis X direction) and defines the insertion angle of the inserting member I when the inserting member I is inserted through the lead-out hole 24. Moreover, as shown below, in the present embodiment, as shown in FIGS. 3 and 4, the perforating member 3 is configured to be guided in the first direction D1 and in the second direction D2 in the interior of the lead-out hole 24 coaxially to an axial center of the lead-out hole 24 (axis X). In this case, as described below, the axial center of the perforation hole H1 of the wall-like tissues T, which is formed with the perforating member 3, coincides with the axial center of the inserting member I inserted through the lead-out hole 24 (or the communicating path F21 of the fixing device F) after the wall-like tissues T are perforated. In this way, a portion of the inserting member I, which passes through the wall-like tissues T, and a portion of the inserting member I, which passes through the lead-out hole 24 of the main body 2 (or the communicating path F21 of the fixing apparatus F) are arranged coaxially. Therefore, while details will be described below, it is suppressed that the main body 2 is lifted or sunk relative to the desired position due to a force received from a portion of the inserting member I which is inserted through the lead-out hole 24 (or the communicating path F21 of the fixing apparatus F). The term "the perforating member 3 is guided in the interior of the lead-out hole 24" means that the perforating member 3 is directly or indirectly guided by the lead-out hole 24 in the lead-out hole 24. In the present embodiment, the perforating member 3 is indirectly guided in the interior of the lead-out hole 24 via a guide hole 51 of the guide member 5. It should be noted that as in an embodiment to be described below (see FIG. 17), the perforating member 3 may be directly guided in the interior of the lead-out hole 24. Moreover, the term "coaxially"

means that the perforating member 3 and the lead-out hole 24 extend on a substantially common axis. In the present embodiment, a direction in which the axial center of the perforating member 3 extends and a direction in which the axial center of the lead-out hole 24 extends are on a substantially identical straight line. It should be noted that as long as the perforating member 3 and the lead-out hole 24 extend on a substantially common axis, the perforating member 3 and the lead-out hole 24 may be curved slightly.

While the angle at which the lead-out hole 24 extends is not limited, as described above, the angle θ (see FIG. 4) formed by the axial center of the lead-out hole 24 (the axis X) and a surface of the wall-like tissues T at the one side Ta (a surface being tangent to a site at which the perforation hole H1 is formed in a case that the surface is curved) may be set to be, for example, 10° to 80°, preferably 20° to 70°, more preferably 30° to 60°. The angle of the lead-out hole 24 may be set so as to correspond to the angle of the communicating path F21 of the fixing device F (for example, the difference in angle relative to the angle of the axial center of the communicating path F21 is less than or equal to 10°, preferably less than or equal to) 5° or may be set so as to be identical to the angle of the communicating path F21 of the fixing device F.

In the present embodiment, the lead-out hole 24 linearly extends for a predetermined length in the axis X direction. The cross-sectional shape of the lead-out hole 24 is not limited as long as the connector 4 and the inserting member I may be insertable through the lead-out hole 24. In the present embodiment, the cross-section perpendicular to the first direction D1 of the lead-out hole 24 is configured to be circular. Moreover, the size of the lead-out hole 24 is not limited as long as the perforating member 3 may be passed through the lead-out hole 24 so as to perforate the wall-like tissues T, and the connector 4 and the inserting member I may be inserted through the lead-out hole 24. In the present embodiment, the inner diameter of the lead-out hole 24 has an inner diameter corresponding to a portion of the connector 4 and the inserting member I, which has the maximum outer diameter (for example, an inner diameter being 100 to 110%, preferably 100 to 105%, more preferably 100 to 103% of the outer diameter of a portion of the connector 4 and the inserting member I, which has the maximum outer diameter).

As shown in FIGS. 2 to 4, the lead-out hole 24 has a first opening 24a facing the wall-like tissues T and a second opening 24b to be an opening opposite to the first opening 24a. An inner space of the lead-out hole 24 is formed between the first opening 24a and the second opening 24b. The first opening 24a faces the wall-like tissues T and opens at the lower surface of the main body portion 21. The second opening 24b opens at the side surface of the main body portion 21.

As shown in FIGS. 2 to 4, the inner surface of the lead-out hole 24 at the second direction D2 side of the lead-out hole 24 has an engaged portion 24c to engage with an engaging portion E of the guide member 5 to be described below. As described below, the engaged portion 24c of the lead-out hole 24 engages with the engaging portion E of the guide member 5 so that detachment of the guide portion 52 of the guide member 5 from the lead-out hole 24 is suppressed. The structure of the engaged portion is not limited as long as the engaged portion can engage with the engaging portion such that detachment of the guide portion 52 from the lead-out hole 24 is suppressed. In the present embodiment, the engaged portion 24c is a female screw to engage the engaging portion E provided as a male screw. However, the engaged portion may be an engaging claw, an engaging concave portion, an engaging convex portion, and the like, in accordance with the structure of the engaging portion. The inner diameter of the engaged portion 24c (a portion of the engaged portion 24c, which has the smallest inner diameter) is larger than the outer diameter of the connector 4 and the inserting member I such that the connector 4 and the inserting member I can exit in the second direction D2 from the second opening 24b of the lead-out hole 24. In a case that the engaged portion 24c is provided as a male screw as in the present embodiment, it is desirable that the engagement between the engaging portion E and the engaged portion 24c is released before the one end 4a of the connector 4 is inserted through the wall-like tissues T (before the one end 4a enters the wall-like tissues T). In other words, the positions of the engaging portion E, the engaged portion 24c, and the one end 4a of the connector 4 are set such that the one end 4a of the connector 4 is positioned on the inner side of the body, relative to the wall-like tissues T, when the engagement between the engaging portion E and the engaged portion 24c is released. In this way, the rotation of the connector 4 following the rotation of the guide member 5 (the rotation when the screw engagement between the engaging portion E and the engaged portion 24c is released) may be prevented when the one end 4a of the connector 4 passes through the wall-like tissues T. Therefore, it is suppressed that the screw engagement between a perforating shaft portion 32 and the connector 4 is released by the rotation of the connector 4 with the connector 4 being placed in the tissues T.

As shown in FIGS. 2 to 4, the lead-out hole 24 has, at the second direction D2 side, a main body-side contact surface 25 to be in contact with a stopper surface 54 of the guide member 5 to restrict the movement of the guide member 5 in the first direction D1 relative to the main body 2. In the present embodiment, the main body-side contact surface 25 is configured by the peripheral portion around the second opening 24b of the lead-out hole 24, which is the surface extending perpendicularly to the axis X direction.

In the present embodiment, as shown in FIGS. 2 to 6, the inserting member lead-out device 1 comprises the guide member 5 being insertable at least partially into the lead-out hole 24, wherein the guide member 5 has the guide hole 51 to guide the perforating member 3 coaxially to the axial center of the lead-out hole 24 (the X axis). The guide member 5 is partially inserted into the lead-out hole 24 of the main body 2 from the second opening 24b side and is attachably/detachably mounted to the main body 2. The guide member 5 guides the perforating member 3 in the first direction D1 (along the axis X) by the guide hole 51. The shape and structure of the guide member 5 are not limited as long as the guide member 5 may be at least partially inserted into the lead-out hole 24 and has the guide hole 51 to guide the perforating member 3 coaxially to the axial center of the lead-out hole 24. As described below, in the inserting member lead-out device 1, the perforating member 3 may be configured to have a part of functions of the guide member 5 (for example, the function of the guide portion 52) and omit the guide member 5 (see FIG. 17).

The guide hole 51 guides the perforating member 3 coaxially to the axial center of the lead-out hole 24 and defines the direction of perforation with the perforating member 3. The perforating member 3 is guided to move in the first direction D1 along the axis X by the guide hole 51 as shown in FIGS. 3 and 4. Therefore, the perforating member 3 can form the perforation hole H1 in the wall-like tissues T along the axis X being coaxial to the axial center of the lead-out hole 24. Both the axial center of the perforation hole H1 and the axial center of the lead-out hole 24 are aligned coaxially along the first direction D1 (along the axis X). In this way, as described above, in a state in which the inserting member I is inserted through the lead-out hole 24 (or the communicating path F21 of the fixing device F), a portion of the inserting member I, which penetrates the wall-like tissues T and passes through the insertion hole H2, and a portion of the inserting member I, which passes through the lead-out hole 24 of the main body 2 (or the communicating path F21 of the fixing device F), are arranged coaxially.

The guide hole 51 is provided through the guide member 5 in the axis X direction, and has an opening at the first direction D1 side and an opening at the second direction D2 side. The shape of the guide hole 51 is not limited as long as the guide hole 51 can guide the perforating member 3 coaxially to the axial center of the lead-out hole 24. In the present embodiment, the guide hole 51 is a hole whose cross-section is circular and is configured to guide the perforating member 3 having a circular cross-section. The size of the guide hole 51 is set to be a size corresponding to the size of the perforating member 3 such that the perforating member 3 can stably move in the first direction D1 when the perforating member 3 passes through the guide hole 51. It should be sufficient to prevent the perforating member 3 from deviating from a predetermined position of perforating the skin due to rattling against the guide hole 51 when the perforating member 3 is guided to the guide hole 51 or to prevent a force from being forcibly acted for insertion/removal of the inserting member 3 into/from the guide hole 51.

In the present embodiment, as shown in FIGS. 2 to 6, the guide member 5 comprises a tubular guide portion 52 to be inserted into the lead-out hole 24 and an extended portion 53 provided to a side in the second direction D2 relative to the guide portion 52, wherein the extended portion 53 extends radially outward relative to an outer periphery of the guide portion 52. Moreover, in the present embodiment, the guide member 5 has a tubular portion 55 with the diameter being larger than that of the guide portion 52. The tubular portion 55 has the above-described stopper surface 54 between the guide portion 52 and the extended portion 53 in the first direction D1.

The guide portion 52 is a portion to be inserted into the lead-out hole 24. In the present embodiment, when the guide portion 52 is inserted into the lead-out hole 24, the guide portion 52 is guided in the lead-out hole 24 such that the guide hole 51 of the guide member 5 is arranged coaxially to the axial center of the lead-out hole 24. In this case, the guide portion 52 is guided in the lead-out hole 24 and the guide member 5 is stably held with respect to the main body 2. Therefore, the perforating member 3 is stably guided along the first direction D1 by the guide hole 51 of the guide member 5. Moreover, the guide portion 52 is guided to the lead-out hole 24 such that the perforating member 3 and the guide member 5 can move in the second direction D2 along the axial center of the lead-out hole 24 (the axis X) after the perforation of the wall-like tissues T with the perforating member 3 is completed and the perforating member 3 is connected to the connector 4 and the inserting member I. In this way, as described below, when the connector 4 and the inserting member I are inserted through the wall-like tissues T from the other side Tb to the one side Ta of the wall-like tissues T (see FIGS. 12 and 13), the connector 4 and the inserting member I are accurately guided along the axis X toward the first opening 24a of the lead-out hole 24. Therefore, the inserting member I penetrates the wall-like tissues T and inserted into the lead-out hole 24 at a desired angle.

In the present embodiment, the guide portion 52 has the shape and size corresponding to the lead-out hole 24 such that the guide portion 52 is stably guided and arranged in the lead-out hole 24. In the present embodiment, the guide portion 52 is formed cylindrically, and the lead-out hole 24 has a cylindrical inner space. It should be noted that the guide portion 52 may have a clearance between the guide portion 52 and the inner surface of the lead-out hole 24 as long as rattling does not occur more than necessary in a state in which the guide portion 52 is arranged in the lead-out hole 24. The inner diameter of the lead-out hole 24 may be set to be 100 to 110%, preferably 100 to 105%, more preferably 100 to 103% of the outer diameter of the guide portion 52, for example.

The length of the guide portion 52 in the axis X direction is not limited. In the present embodiment, the length of the guide portion 52 (and the lead-out hole 24) is preferably set such that the guide portion 52 is guided to the lead-out hole 24 during the time from a state in which the perforation hole H1 is formed with the perforating member 3 and the connector 4 is connected to the perforating member 3 at the other side Tb of the wall-like tissues T (see FIG. 11) to a state in which the perforating member 3 and the connector 4 move in the second direction D2 and the one end 4a of the connector 4 reaches the first opening portion 24a of the lead-out hole 24. In this case, during the time from the state in which the connector 4 is connected to the perforating member 3 to the state in which the connector 4 enters the lead-out hole 24, the connector 4 and the inserting member I move along the axis X coaxially to the axis of the lead-out hole 24. Therefore, the connector 4 and the inserting member I can be surely moved into the lead-out hole 24. The connector 4 is guided in the lead-out hole 24 after the connector 4 enters the first opening 24a of the lead-out hole 24. Therefore, the connector 4 and the inserting member I moves along the axis X in the lead-out hole 24 even when the guide member 5 and the perforating member 3 move so as to be inclined relative to the axial center of the lead-out hole 24 after the guide portion 52 is removed from the lead-out hole 24 in the second direction D2. Therefore, the connector 4 and the inserting member I can be stably led out.

As shown in FIGS. 2 to 4, the guide member 5 has the engaging portion E to engage with the main body 2 to suppress the guide portion 52 of the guide member 5 from detaching from the lead-out hole 24. By providing the engaging portion E, detaching of the guide member 5 from the lead-out hole 24 is suppressed even when a force is applied to the guide member 5 in the second direction D2 when the wall-like tissues T are perforated with the perforating member 3. Therefore, the perforating member 3 can be moved stably in the first direction D1 (see FIGS. 9 and 10). The engaging portion E engages the main body 2 such that the movement, relative to the main body 2, of the guide member 5 in the second direction D2 is restricted. Preferably, the engaging portion E is configured to restrict the movement, relative to the main body 2, of the guide member 5 in both the first direction D1 and the second direction D2. In the present embodiment, the engaging portion E is a male screw provided to the end at the second direction D2 side of the guide portion 52 and engages a female screw provided to the engaged portion 24c of the main body 2. However, the shape and structure of the engaging portion are not limited as long as the engaging portion can engage with the main body 2 to suppress the guide portion 52 of the guide member 5 from detaching from the lead-out hole 24. For example, the engaging portion may be an engaging claw, an engaging concave portion, and an engaging convex portion, and the like, having a structure according to the structure of the engaged portion of the main body 2 to engage with the engaged portion in the axis X direction.

The engaging portion E is engaged so as to allow releasing of the engagement with respect to the engaged portion 24c. In this way, the guide member 5 is removed from the main body 2 after the perforation of the wall-like tissues T with the perforating member 3 is completed. Therefore, it is possible to lead out the connector 4 and the inserting member I into the lead-out hole 24 (see FIGS. 11 to 13).

As shown in FIGS. 2 to 6, the extended portion 53 is provided at the second direction D2 side of the guide portion 52 and extends radially outward with respect to the outer periphery of the guide portion 52. The extended portion 53 improves the operability when perforating the wall-like tissues T with the perforating member 3. Specifically, the perforating member 3 can be pushed in the first direction D1 while placing a finger on the surface of the extend portion 53 at the first direction D1 side. In other words, the perforating member 3 functions as a plunger of an injector and the extended portion 53 functions as a flange portion of a syringe of the injector. Therefore, it is easy to apply a force to the perforating member 3, facilitating the perforation of the wall-like tissues T with the perforating member 3. Moreover, the extended portion 53 can also improve the operability when attaching/detaching the guide portion 52 to/from the main body 2. Specifically, the guide member 5 can be rotated while holding the extended portion 53 when carrying out the screw engagement/release of the screw engagement between the engaging portion E and the engaged portion 24 constituting the screw structure. In this way, the guide member 5 can easily be rotated around the axis X. Therefore, the attachment/detachment of the guide member 5 to/from the main body 2 is facilitated.

Figure 5:
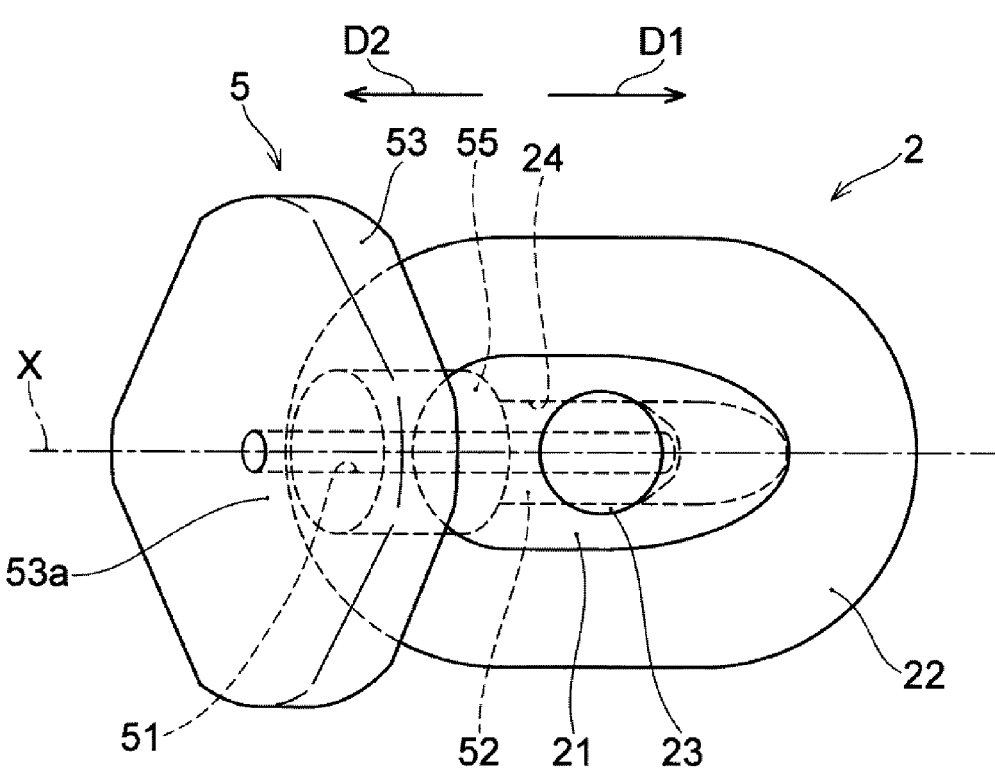
FIG. 5 is a top view showing a state in which a guide member is assembled to a main body of the inserting member lead-out device.
Figure 6:
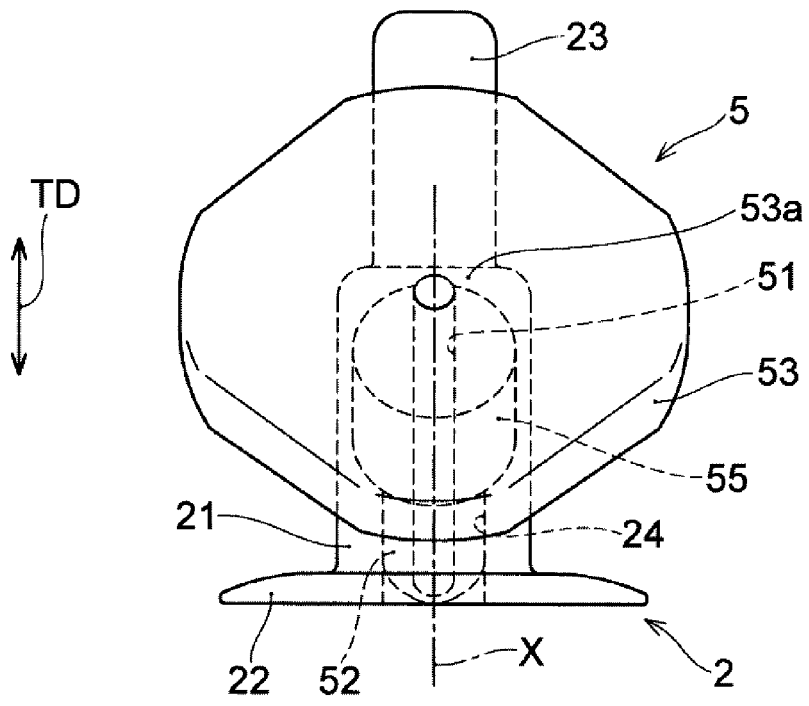
FIG. 6 is a front view showing a state in which the guide member is assembled to the main body of the inserting member lead-out device.

In the present embodiment, as shown in FIGS. 5 and 6, the extended portion 53 is provided at the second direction D2 side with respect to the tubular portion 55 of the guide member 5 and the extended portion 53 is configured to extend from the whole part in the peripheral direction of the tubular portion 55. However, the shape of the extended portion 53 is not limited, so that the extended portion 53 may be configured to protrude from only a part in the peripheral direction.

The perforating member 3 is movable relative to the main body 2 and is a member to form the perforation hole H1 in the wall-like tissues T. While a tip portion 31 of the perforating member 3 is formed in the shape of a needle in the present embodiment, the tip portion 31 does not have to be needle-shaped as long as the tip portion 31 can form the perforation hole H1 in the wall-shaped tissues T.

Figure 11:
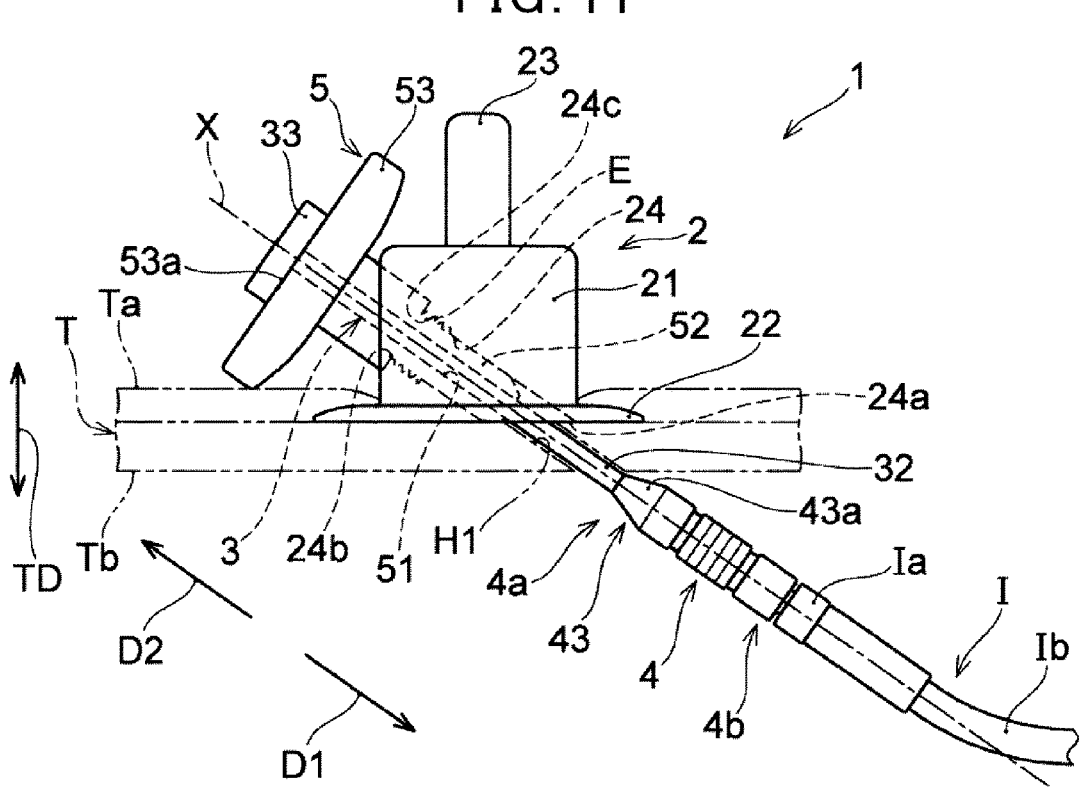
FIG. 11 is a schematic view showing a state in which the perforating member, the connector, and the inserting member are connected from the state shown in FIG. 10.
Figure 12:
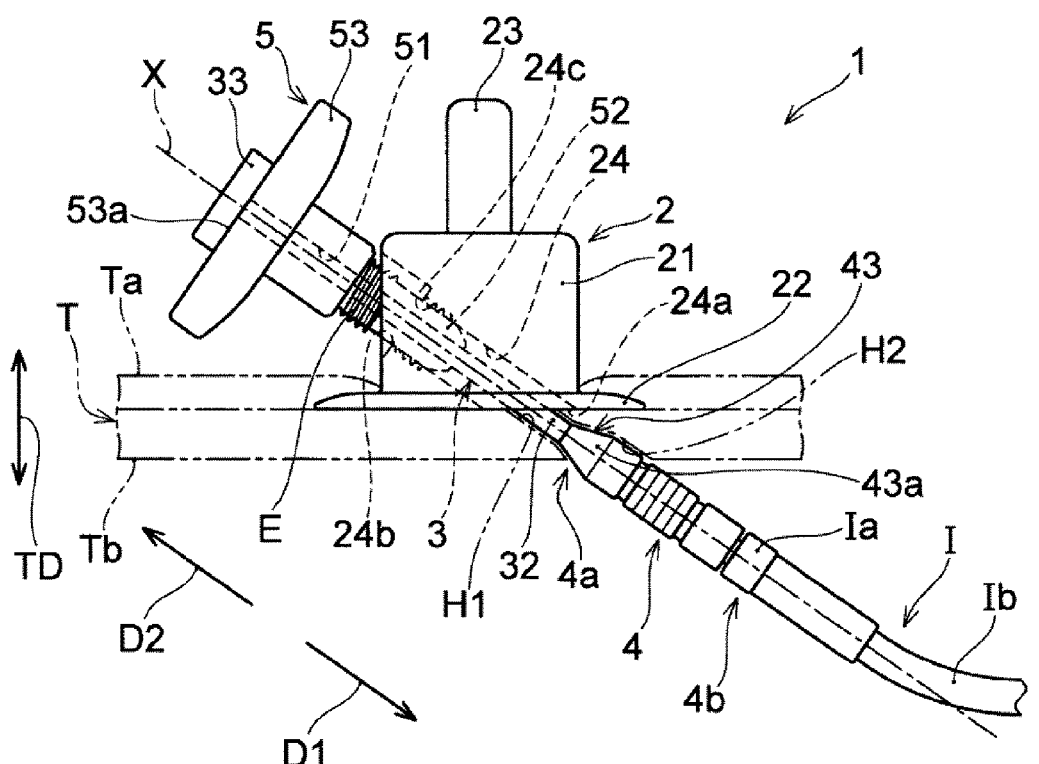
FIG. 12 is a schematic view showing a state in which the connector partially enters the wall-like tissues and partially widens a perforation hole from the state shown in FIG. 11.
Figure 13:
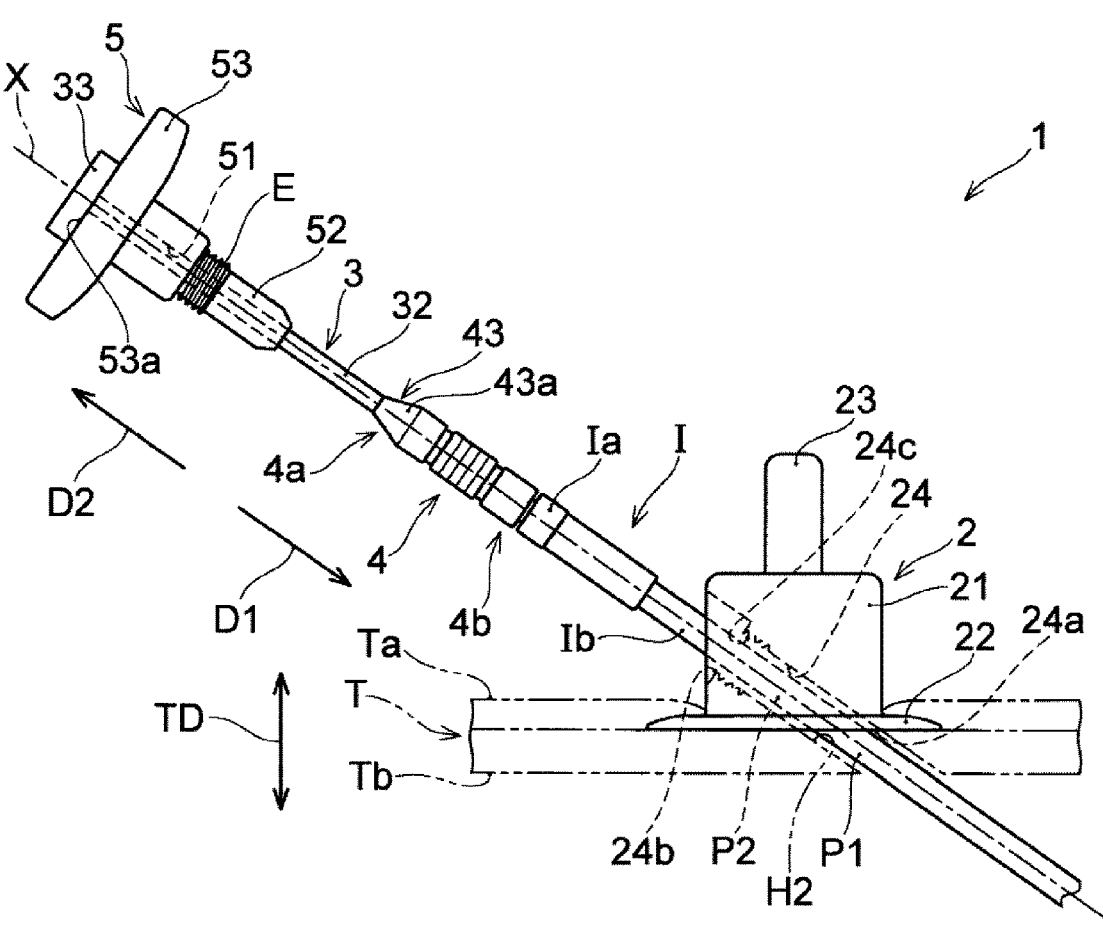
FIG. 13 is a schematic view showing a state in which the inserting member is led out to one side of the wall-like tissues from the state shown in FIG. 12.

In the present embodiment, as shown in FIGS. 3, 4, 9, and 10, at the time of perforation of the wall-like tissues T, the perforating member 3 moves in the first direction D1 relative to the main body 2 and the guide member 5, thereby protruding in the first direction D1 along the axis X from the first opening 24a of the lead-out hole 24. In this way, the perforation hole H1 is formed in the wall-like tissues T. Moreover, after forming the perforation hole H1, as shown in FIGS. 11 to 13, the perforating member 3 is indirectly connected to the inserting member I via the connector 4. When the perforating member 3 moves in the second direction D2 and is withdrawn from the wall-like tissues T in the second direction D2, the perforating member 3 leads out the inserting member I from the other side Tb to the one side Ta of the wall-like tissues T.

As shown in FIGS. 2 to 4, the perforating member 3 has the tip portion 31, and the perforating shaft portion 32 to be a part inserted into the wall-like tissues T, wherein the perforating shaft portion 32 is adjacent to the tip portion 31 in the length direction of the perforating member 3. Moreover, the perforating member 3 has a connecting portion C to be connected to the connector 4.

The tip portion 31 is a portion provided at the end of the perforating member 3 at the first direction D1 side in the longitudinal direction. The perforating member 3 is moved in the first direction D1, thereby the tip portion 31 perforates the wall-like tissues T to form the perforation hole H1 passing through the wall-like tissues T from the one side Ta to the other side Tb of the wall-like tissues T. In the present embodiment, the tip portion 31 is formed in the shape of a needle to be tapered toward the tip end of the tip portion 31. However, as long as the tip portion 31 can form the perforation hole H1 in the wall-like tissues T, for example, the tip portion 31 may be a tubular shape and does not need to have a tapered shape, or the tip end of the tip portion 31 does not have to be sharp.

The perforating shaft portion 32 is adjacent to the tip portion 31 in the length direction (the axis X direction) of the perforating member 3, and is inserted into the wall-like tissues T. The perforating shaft portion 32 has a length in the axis X direction so as to pass through the wall-like tissues T, and at least a part of the perforating shaft portion 32 is inserted into the wall-like tissues T. The shape of the perforating shaft portion 32 is not limited as long as the perforating shaft portion 32 can perforate the wall-like tissues T. In the present embodiment, the perforating shaft portion 32 is formed such that a cross-section of the perforating shaft portion 32 perpendicular to the longitudinal direction is circular.

The maximum dimension of the perforating shaft portion 32 in the radial direction of the inserting member I (a direction perpendicular to the longitudinal direction of the inserting member I) is smaller than the outer diameter of the inserting member I. In the present embodiment, the perforating shaft portion 32 is formed in the shape of a cylinder having the same outer diameter along the longitudinal direction, and, as shown in FIGS. 2 to 4, the outer diameter of the perforating shaft portion 32 is configured to be smaller than the outer diameter of the inserting member I. The maximum dimension of the perforating shaft portion 32 is smaller than the outer diameter of the inserting member I, thereby the perforation hole H1 can be formed with a force smaller than that in a case of opening a perforation hole in the wall-like tissues T with a perforating shaft portion having the same dimension as that of the outer diameter of the inserting member I. Here, the term "maximum dimension of the perforating shaft portion 32" is the maximum dimension of a portion to be entered into the wall-like tissues T in the perforating shaft portion 32. In a case that the outer diameter of the inserting member I including the coupling portion Ia is same in the longitudinal direction of the inserting member I, "outer diameter of the inserting member I" refers to the outer diameter of the inserting member I. In a case that the outer diameter of the inserting member I including the coupling portion Ia partially varies in the longitudinal direction, "outer diameter of the inserting member I" refers to a portion having maximum outer diameter in the portion of the inserting member I which is led out from the other side Tb to the one aide Ta of the wall-like tissues. The maximum dimension of the perforation shaft portion 32 of the perforation member 3 is not limited. It should be sufficient that the diameter of the perforation shaft portion 32 of the perforation member 3 have a desired size to perforate the wall-like tissues T without breaking and exert a force necessary to pull out the connector 4 and the inserting member I when connected to the connector 4. The diameter of the perforation shaft portion 32 may be set to be, for example, 5 to 70%, preferably 20 to 60%, more preferably 35 to 50% of the outer diameter of the inserting member I.

Moreover, in the present embodiment, as shown in FIGS. 2 to 4, the perforating member 3 has a stopper portion 33 to restrict an amount of protrusion from the main body 2 of the perforating member 3 to be within a predetermined range. The stopper portion 33 restricts an amount of protrusion (see FIG. 4) of the perforating member 3 from the main body 2 (the first opening 24*a* of the lead-out hole 24) to be within a predetermined range when the wall-like tissues T are perforated from the one side Ta toward the other side Tb with the perforating member 3. In this way, the position at which the tip portion 31 of the perforating member 3 reaches when the wall-like tissues T are perforated with the perforating member 3 from the outside to the inside of the body, for example, can be easily controlled. Therefore, the risk of damaging the tissues such as other organs and the like by the amount of protrusion of the perforating member 3 increasing can be reduced. "The predetermined range" may be set to be, for example, a range such that, when the perforating member 3 enters the wall-like tissues T, the tip portion of the perforating member does not reach the tissues such as the internal organs and the like, other than the tissues to be perforated. This predetermined range is changed as needed in accordance with a target to be perforated (a site of the living body to be perforated, physique, age, gender, and the like).

In the present embodiment, the stopper portion 33 is in contact with a contacting portion 53*a* provided in the guide member 5, thereby restricting the amount of protrusion of the perforating member 3 from the main body 2 to be within a predetermined range. In the present embodiment, the stopper portion 33 extends with respect to the perforating shaft portion 32 in a direction perpendicular to the axis X direction. More specifically, the extended stopper portion 33 is configured to be in contact with the contacting portion 53*a* provided to the peripheral portion around an opening at the second direction D2 side of the guide hole 51 of the guide member 5 (in the present embodiment, an end surface of the extended portion 53 at the second direction D2 side).

The shape of the stopper portion is not limited as long as the amount of protrusion of the perforating member 3 from the main body 2 can be restricted to be within a predetermined range. The shape of the stopper portion may be a disc shape or a rectangular plate shape. In the present embodiment, the stopper portion 33 is provided at the end of the perorating member 3 at the second direction D2 side. However, the stopper portion may be provided at a part other than the end of the perforating member 3 (for example, at a position between the end of the perforating member 3 at the second direction D2 side and the center portion of the perforating shaft portion 32, and the like).

In the present embodiment, the stopper portion 33 and the guide member 5 are engaged with each other in the axis X direction. In this way, when withdrawing the perforating member 3 from the wall-like tissues T after the perforation hole H1 is formed in the wall-like tissues T with the perforating member 3, as shown in FIGS. 12 and 13, by moving the guide member 5 in the second direction D2 relative to the main body 2, it is possible to also simultaneously move the perforating member 3 in the second direction D2. Then, at this time, the connector 4 and the inserting member I are led out from the other side Tb to the one side Ta of the walled-tissues T. Therefore, removing of the guide member 5 from the main body 2, withdrawing the perforating member 3 from the wall-like tissues T, and leading-out of the inserting member I can be carried out simultaneously, so that the operability improves, leading to the shortening of the operation time.

The connecting portion C is a part to be connected to the connector 4. The position of the connecting portion C is not limited as long as the connecting portion C is provided to a position at which the connecting portion C can be connected to the connector 4 at the other side Tb of the wall-like tissues T after the wall-like tissues T are perforated with the perforating member 3. In the present embodiment, as shown in FIGS. 2 to 4, the connecting portion C is provided to a position adjacent to the tip portion 31 at the second direction D2 side. The shape and structure of the connecting portion C are not limited as long as the connecting portion C can be connected to the connector 4 such that the inserting member I can be led out from the wall-like tissues T. In the present embodiment, the connecting portion C is a male screw provided to the outer periphery of the perforating shaft portion 32. The connecting portion C engages a female screw provided in the first connecting portion 41 of the connector 4. However, the connecting portion C may be an engaging claw, an engaging concave portion, an engaging convex portion, and the like that have a structure according to the structure of the first connecting structure 41 of the connector 4 and engage with the first connecting portion 41 in the axis X direction.

The connector 4 connects the perforating member 3 and the inserting member I. In the present embodiment, the connector 4 is connected to the perforating member 3 and the inserting member I at the other side Tb of the wall-like tissues T in a state in which the perforating member 3 perforates the wall-like tissues T as shown in FIG. 11. As described below, as shown in FIGS. 12 and 13, the perforating member 3 and the inserting member I connected via the connector 4 at the other side Tb of the wall-like tissues T integrally moves toward the one side Ta of the wall-like tissues T through the perforation hole H1 (the insertion hole H2) by the movement of the perforating member 3 in the second direction D2. In this way, the inserting member I is led out to the one side Ta of the wall-like tissues T.

Figure 7:
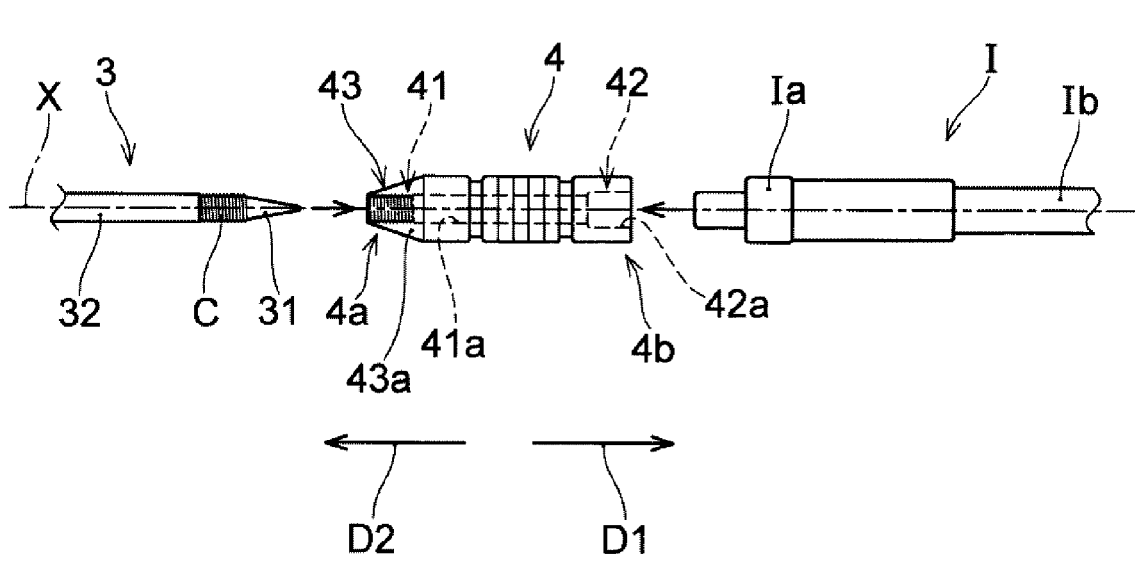
FIG. 7 is a view showing a state before the perforating member, a connector, and the inserting member are connected.
Figure 8:
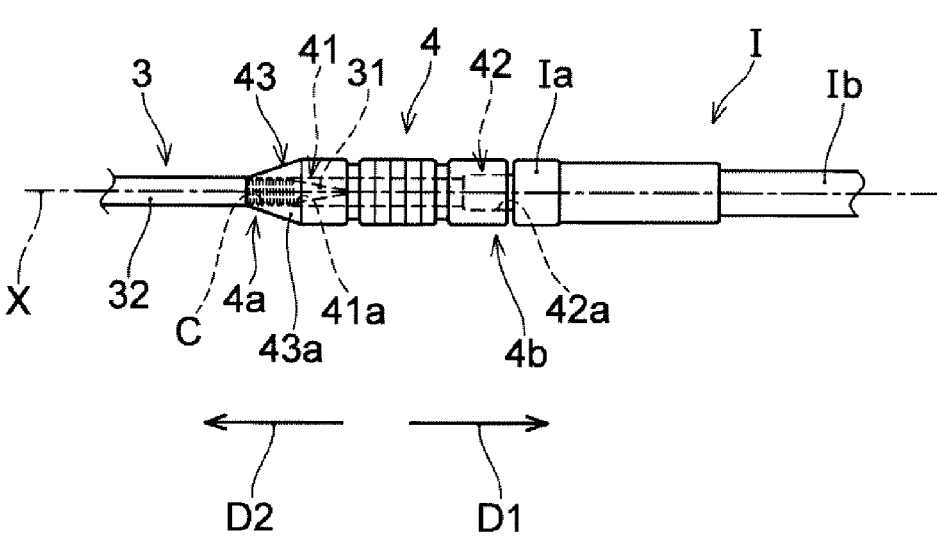
FIG. 8 is a view showing a state in which the perforating member, the connector, and the inserting member are connected.

As shown in FIGS. 7 and 8, the connector 4 comprises the first connecting portion 41 being connectable to the perforating member 3 at the one end 4*a* side and the second connecting portion 42 being connectable to the inserting member I at the other side 4*b*. The overall shape of the connector is not limited as long as the connector can connect the perforating member 3 and the inserting member I. In the present embodiment, the connector 4 has a substantially cylindrical shape.

The first connecting portion 41 is a part to be connected to the perforating member 3. As shown in FIGS. 7 and 8, in the present embodiment, the first connecting portion 41 has a female screw to be connected by screwing with the connecting portion C of the perforating member 3, which is constituted by a male screw. More specifically, the first connecting portion 41 has a female screw provided on the inner surface of a tubular hollow portion 41*a* provided along the axial center of the connector 4 at the one end 4*a* side of the connector 4. As shown in FIG. 8, the tubular hollow portion 41*a* of the first connecting portion 41 is formed in a size that can accommodate not only the connecting portion C of the perforating member 3 but also the tip portion 31 of the perforating member 3.

The structure of the first connecting portion 41 is not limited as long as the first connecting portion 41 is configured to prevent the connection between perforating member 3 and the connector 4 being released when the perforating member 3 moves in the second direction D2 with the perforating member 3, the connector 4, and the inserting member I being connected. For example, the first connecting portion may be another mechanical connecting structure such as an engaging claw and the like, or may be configured to be connected by a magnetic force.

The second connecting portion 42 is a part to be connected to the inserting member I. In the present embodiment, the second connecting portion 42 is connectable to the coupling portion Ia provided at the end of the inserting member I. More specifically, at the end of a driveline being the inserting member I, a male plug (the coupling portion Ia) to be plugged into and connected to a drive portion (a power supply) of the driveline is provided, and the second connecting portion 42 is configured to mate and connect with the above-mentioned male plug (the coupling portion Ia). For example, an engaging protrusion (not shown) is provided on the outer periphery of the male plug being the coupling portion Ia, and the second connecting portion 42 may be constituted by a tubular hollow portion 42a, the inner surface of which has an engaging concave portion (not shown) to engage with the engaging protrusion of the coupling portion Ia.

The structure of the second connecting structure 42 is not limited as long as the second connecting portion 42 is configured to prevent the connection between the connector 4 and the inserting member I being released when the perforating member 3 moves in the second direction D2 with the perforating member 3, the connector 4, and the inserting member I being connected. For example, the second connecting portion may be another mechanical connecting structure such as a screw, an engaging claw and the like, or may be configured to be connected by a magnetic force. While the second connecting portion 42 is configured to be connect the connector 4 being separated from the inserting member I to the end of the inserting member I in the present embodiment, the connector may be connected to the inserting member I in advance.

Besides, in the present embodiment, the connector 4 has a widened portion 43 at the one end 4a side. The widened portion 43 will be described below.

As described above, in the inserting member lead-out device 1 of the present embodiment, as shown in FIGS. 3 and 4, the perforating member 3 is configured to be guided in the first direction D1 and in the second direction D2 in the interior of the lead-out hole 24 coaxially to the axial center of the lead-out hole 24 (the axis X). Moreover, the lead-out hole 24 has a size allowing the connector 4 and the inserting member I to be inserted through the lead-out hole 24 when the perforating member 3 is moved in the second direction D2 in a state in which the perforating member 3 is connected to the connector 4 with the connector 4 being connected to the inserting member I at the other side Tb of the wall-like tissues T. In this way, a portion of the inserting member I, which penetrates the wall-like tissues T and passes through the insertion hole H2, and a portion of the inserting member I, which passes through the lead-out hole 24 of the main body 2, are arranged coaxially. Therefore, it is suppressed that the main body is lifted or sunk relative to the desired position of the main body 2 by receiving a force from a portion of the inserting member I, which is inserted through the lead-out hole 24.

Moreover, the perforating member 3 is guided to the lead-out hole 24 such that the perforating member 3 moves in the second direction D2 along the axial center of the lead-out hole 24 (the axis X), as shown in FIGS. 12 and 13, after the perforation of the wall-like tissues T with the perforating member 3 is completed and the perforating member 3 is connected to the connector 4 and the inserting member I (see FIG. 11). In this way, when the connector 4 and the inserting member I are inserted through the wall-like tissues T from the other side Tb to the one side Ta of the wall-like tissues T, the connector 4 and the inserting member I are accurately guided along the axis X toward the first opening 24a of the lead-out hole 24. Therefore, the inserting member I penetrates the wall-like tissues T and is inserted into the lead-out hole 24 at a desired angle. As described above, the inserting member lead-out device 1 of the present embodiment can accurately and easily lead out the inserting member I from the wall-like tissues T.

Below, the above-described operational effects will be described in more detail.

As described above, since the perforating member 3 is guided in the interior of the lead-out hole 24 coaxially to the axial center of the lead-out hole 24, the perforation hole H1 formed with the perforating member 3 is formed as a through hole coaxial to the axial center of the lead-out hole 24 as shown in FIG. 4. Therefore, deviation is unlikely to occur between the angle at which the perforation hole H1 formed through the wall-like tissues T extends and the angle of the axial center of the lead-out hole 24 at the one side Ta of the wall-like tissues T. Therefore, as shown in FIG. 13, when the inserting member I is led out from the other side Tb to the one side Ta of the wall-like tissues T, a portion P1 of the inserting member I which passes through the insertion hole H2 penetrating the wall-like tissues T (see FIG. 13), and a portion P2 of the inserting member I which passes through the lead-out hole 24 (or the communicating path F21 of the fixing device F) are aligned along the axis X. Therefore, it is suppressed that the main body 2 or the fixing device F is lifted or sunk relative to the surface of the wall-like tissues T caused by the fact that the portion P1 of the inserting member I which passes through the insertion hole H2 penetrating the wall-like tissues T and the portion P2 of the inserting member I which passes through the lead-out hole 24 extend at different angles. Particularly, when perforating the perforation hole H1 at a predetermined angle with respect to the wall-like tissues of the human body, in a case that the predetermined angle is an angle inclined with respect to the wall-like tissues of the human body, particularly in a case that the inclined angle is 30 to 60 degrees, the perforation operation is difficult by using a conventionally used guiding-in member with an arc shaped tip for passing through the wall-like tissues T while expanding the incision site, such as a tunneller, since the guiding-in member slides on the skin surface. By using the inserting member lead-out device 1 of the present embodiment, sliding of the perforating member 3 on the upper surface of the skin is prevented, and, moreover, the perforation operation is facilitated owing to the above-described effects. Therefore, in a case that the fixed device F is used as a skin button, the driveline can be led out at an inclined angle, preventing the driveline from getting in the way under the clothes compared to a case in which the driveline is led out perpendicularly to the skin.

Below, this point will be described in more detail. In a case that a perforation hole to pass through the inserting member I is formed with a perforating member such as a tunneler, unlike the inserting member lead-out device 1 of lead-out device 1 is installed at a predetermined position of the wall-like tissues T, specifically, at a predetermined position of the abdomen of the patient. It should be noted that the inserting member lead-out device 1 is eventually replaced by the fixing device F after the driveline I is led out.

The installation of the inserting member lead-out device 1 into the abdomen is carried out by incising the skin, which is a part of the wall-like tissues T, and slipping the flange portion 22 of the main body 2 beneath the skin. The main body portion 21 and the flange portion 22 of the main body 2 have the shape and size corresponding to the fixing portion F1 and the communicating portion F2 of the fixing device F (see FIG. 1), and this installation operation ensures that the fixing device F is surely mounted later.

Figure 9:
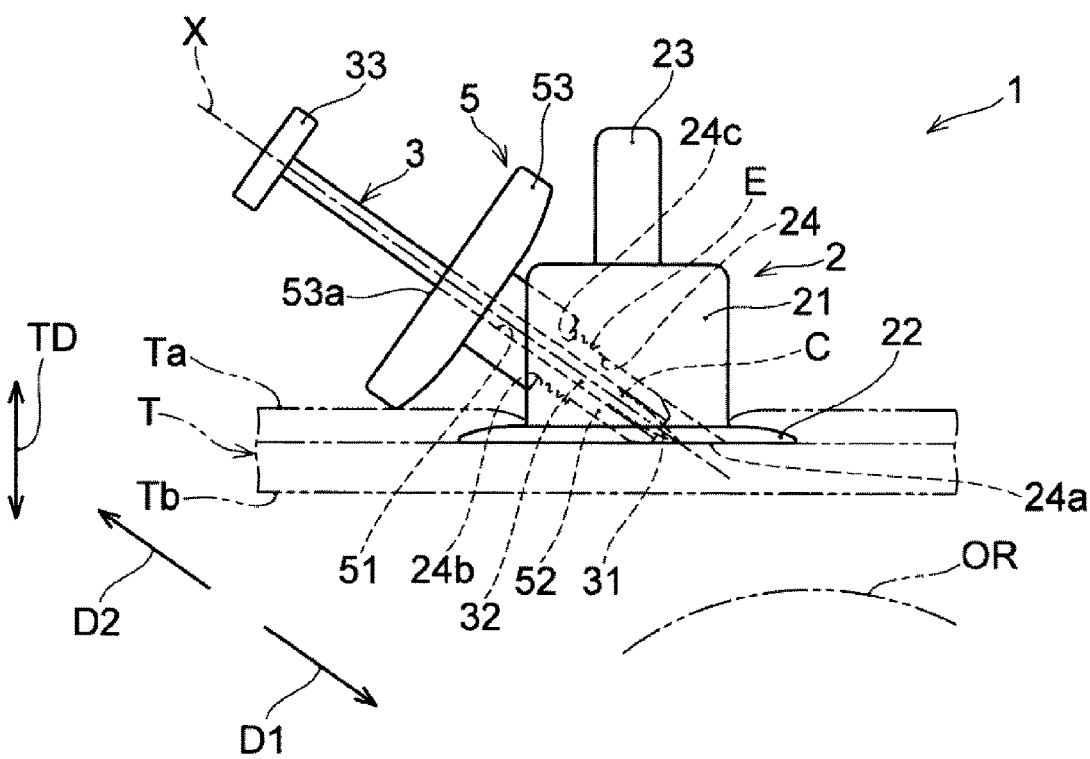
FIG. 9 is a schematic view showing a state in which the main body of the inserting member lead-out device is arranged in the wall-like tissues before the perforating member perforates the wall-like tissues.

As shown in FIG. 9, in a state in which the main body 2 being installed in the wall-like tissues T, the guide portion 52 of the guide member 5 is inserted into the lead-out hole 24 of the main body 2, and the engaging portion E, which is a male screw, of the guide member 5 is screwed into the engaged portion 24c, which is a female screw, of the main body 2. Therefore, the guide member 5 is fixed to the main body 2 with the movement in the axis X direction being restricted. Moreover, the perforating member 3 is inserted into the guiding hole 51 of the guide member 5, and the tip portion 31 of the perforating member 3 does not protrude in the first direction D1 from the first opening 24a of the lead-out hole 24.

Figure 10:
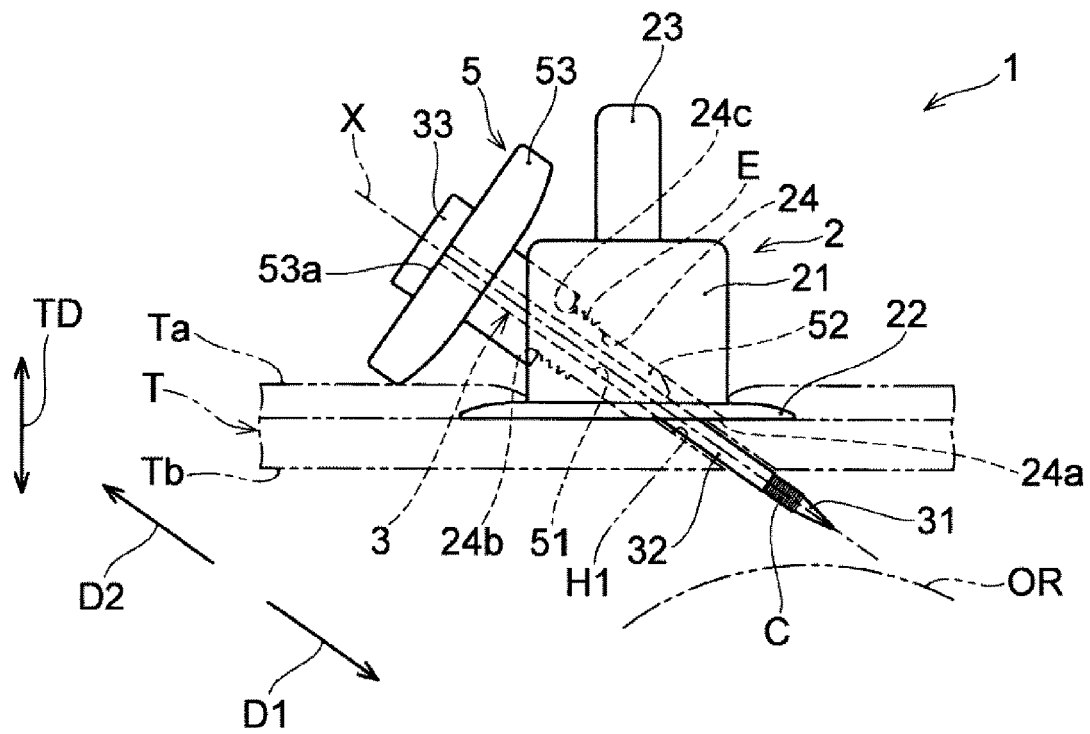
FIG. 10 is a schematic view showing a state in which the perforating member perforates the wall-like tissues from the state shown in FIG. 9.

After installing of the main body 2 into the wall-like tissues T is completed, as shown in FIG. 10, the perforation hole H1 is formed in the wall-like tissues T with the perforating member 3. Specifically, in a state in which the grip portion 23 of the main body 2 is held so as not to tilt the main body 2, the perforating member 3 is pushed in the first direction D1. Since the perforating member 3 is guided by the guide hole 51 to move coaxially to the lead-out hole 24, the perforation hole H1 extending coaxially to the lead-out hole 24 is formed in the wall-like tissues T.

At this time, a finger of the operator is placed on the surface on the first direction D1 side of the extended portion 53 of the guide member 5, and the perforating member 3 is pushed in the first direction D1 by another finger of the same hand. In this way, the perforating member 3 can be pushed into the wall-like tissues T with a simple operation such as an operation of a plunger of an injector. The perforating member 3 is thinner than the driveline I and can easily pass through the skin and the muscular layer.

When the perforating member 3 moves in the first direction D1 by a predetermined amount, the stopper portion 33 of the perforating member 3 comes into contact with the contacting portion 53a provided on the surface at the second direction D2 side of the extended portion 53, and the perforating member 3 stops. Therefore, the perforating member 3 accidentally perforating deep into the wall-like tissues T is suppressed. In this way, tissues OR, such as other organs inside of the body, being damaged by the tip portion 31 of the perforating member 3 is suppressed.

When the perforating member 3 reaches the other side (inside of the body) Tb of the wall-like tissues T, as shown in FIG. 11, the perforating member 3 and the driveline I are connected via the connector 4 by the operator inside the body of a patient. Specifically, the perforating member 3 and the connector 4 are connected by screwing the first connecting portion 41, which is a female screw, of the connector 4 to the connecting portion C, which is a male screw, of the perforating member 3. Moreover, the connector 4 and the driveline I are connected by plugging the coupling portion Ia being a male plug provided at the end of the driveline I into the second connecting portion 42 being a female plug provided at the other end 4b of the connector 4. In this way, the perforating member 3, the connector 4, and the driveline I are integrally connected in the axis X direction.

After the perforating member 3 and the driveline I are connected via the connector 4, as shown in FIG. 12, the guide member 5 is removed from the main body 2. Specifically, the guide member 5 is rotated around the axis X, thereby the screw engagement between the engaging portion E of the guide member 5 and the engaged portion 24c of the main body 2 is released. Therefore, it is possible to withdraw the guide portion 52 of the guide member 5 from the lead-out hole 24. When the guide portion 52 of the guide member 5 is withdrawn from the lead-out hole 24 and the guide member 5 further moves in the second direction D2, the perforating member 3 being engaged with the guide member 5 in the axis X direction at a part of the stopper portion 33 also moves in the second direction D2. In this way, the connector 4 and the inserting member I are also moved in the second direction D2 by the perforating member 3.

When the connector 4 moves in the second direction D2, as shown in FIG. 12, the tapered portion 43a provided at the one end 4a side of the connector 4 widens the perforation hole H1 in the radial direction. When the connector 4 further moves in the second direction D2, the perforation hole H1 is widened by the tapered portion 43a of the connector 4 to a size that allows the driveline I to pass therethrough, forming the insertion hole H2 (see FIG. 13). When the connector 4 and the driveline I pass through the insertion hole H2, as shown in FIG. 13, the driveline I passes through the lead-out hole 24 of the main body 2 and is led out to the outside of the body.

Figure 14:
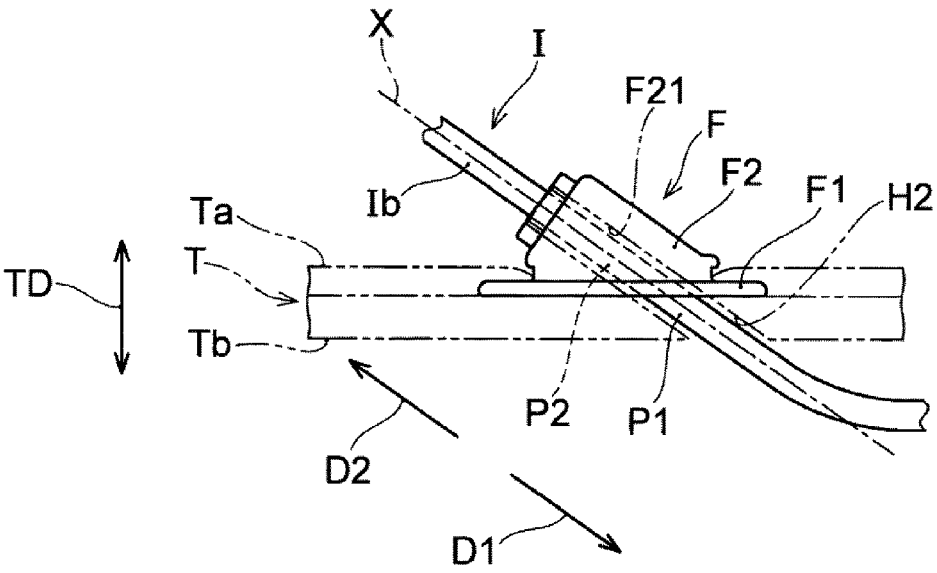
FIG. 14 is a schematic view showing a state in which the main body is removed from the wall-like tissues, and the fixing device through which the inserting member is inserted is fixed to the wall-like tissues from the state shown in FIG. 13.
Figure 15:
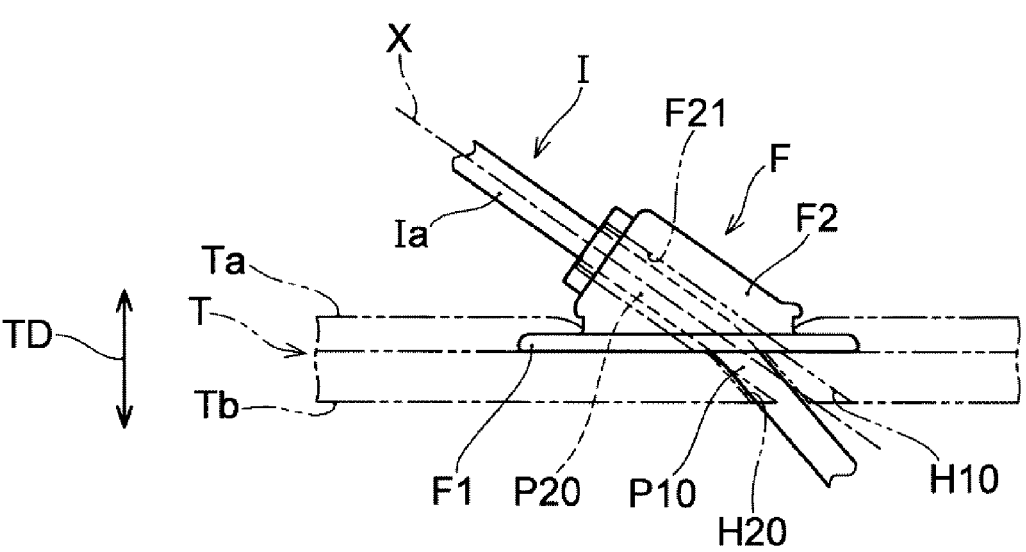
FIG. 15 is a reference view showing the fixing device in which the inserting member is inserted through the insertion hole formed at an angle deviating relative to that for an ideal insertion hole extending in parallel with a communicating path of the fixing device.
Figure 16:
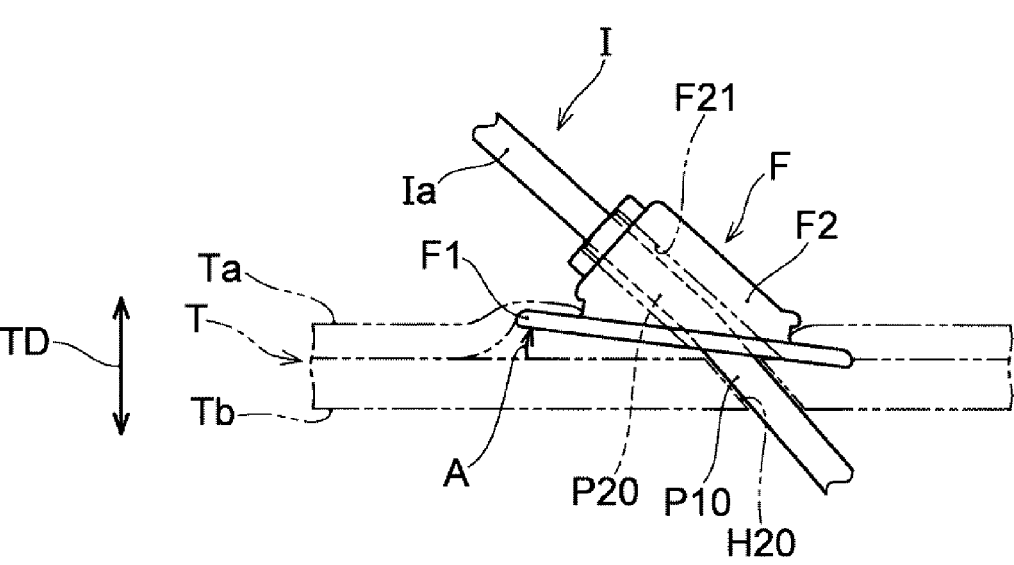
FIG. 16 is a reference view showing a state in which skin is lifted in the fixing device shown in FIG. 15.

After the driveline I is led out to the outside of the body, the connection between the connector 4 and the inserting member I is released, the main body 2 is removed from the wall-like tissues T, and, as shown in FIG. 14, the fixed device F is fixed to a location at which the main body 2 is provided. The communicating path F21 of the fixing device F is inclined at the same angle as the lead-out hole 24 of the main body 2, and the communicating path F21 of the fixing device F and the insertion hole H2 extend coaxially. Specifically, as shown in FIG. 13, the driveline I extends linearly along the communicating path F21 and the insertion hole H2. Therefore, it is suppressed that the fixing device F is lifted or sunk with respect to the wall-like tissues T caused by the fact that the portion P1 of the inserting member I which passes through the insertion hole H2 and the portion P2 of the inserting member I which passes through the communicating path F21 extend at different angles.

Second Embodiment

In a second embodiment, unlike in the first embodiment, a guide member 5 is not provided, and a perforating member 5 is directly guided to a lead-out hole 24 of a main body 2. Except for the guide member 5 being not provided, basically the second embodiment can be configured in the same manner as the first embodiment, so that explanations of the same configuration will be omitted. Matters explained in the first embodiment can be applied in the second embodiment.

Figure 17:
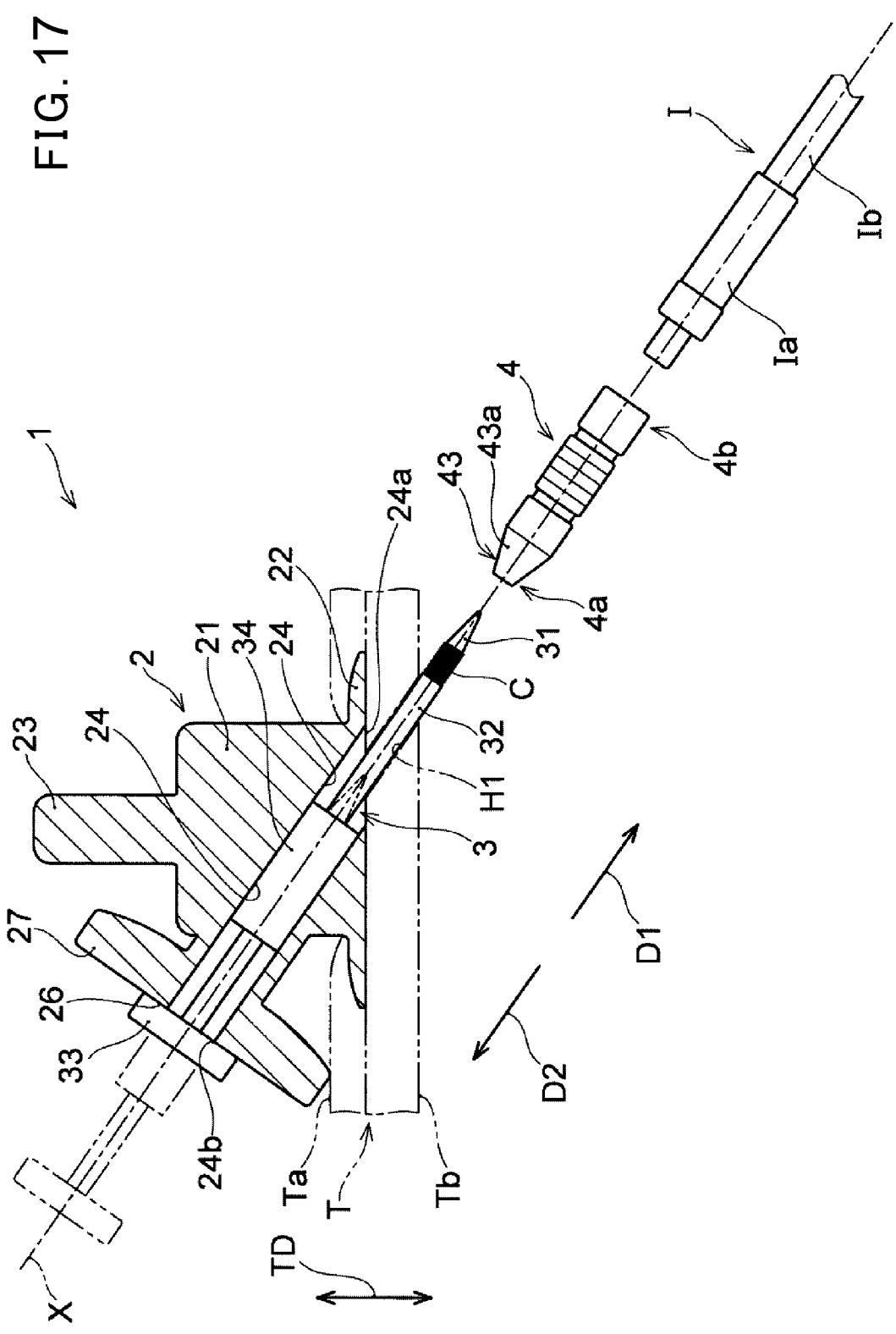
FIG. 17 is a view showing the inserting member lead-out device of a second embodiment of the present invention.

In the present embodiment, as shown in FIG. 17, the perforating member 3 has a guide portion 34 to be guided to the lead-out hole 24. The lead-out hole 24 has an inner diameter corresponding to the outer diameter of the guide portion 34 (for example, an inner diameter being 100 to 110%, preferably 100 to 105%, more preferably 100 to 103% of the maximum outer diameter of the guide portion 34). The guide portion 34 is provided at a position so as not to protrude in a first direction D1 relative to a first opening 24*a* of the lead-out hole 24 when wall-like tissues T are perforated with the perforating member 3. In the present embodiment, the guide portion 34 of the perforating member 3 has the same function as the guide portion 52 of the guide member 5 of the first embodiment.

In the present embodiment, the main body 2 has a contacting portion 26 to be in contact with a stopper portion 33 of the perforating member 3. The contacting portion 26 is configured by the peripheral portion around an opening at a second direction D2 side of the lead-out hole 24. The contacting portion 26 of the main body 2 has the same function as the contacting portion 53*a* of the guide member 3 in the first embodiment. In the second embodiment, the main body 2 has a flange portion 27, and the contacting portion 26 is provided to the end surface at the second direction D2 side of the flange portion 27.

The features other than the above are basically the same as in the first embodiment, and the inserting member lead-out device 1 of the second embodiment can achieve the same effect as the inserting member lead-out device 1 of the first embodiment.

The invention claimed is:

1. An inserting member lead-out device for inserting a linear inserting member through wall-like tissues of the living body, the inserting member lead-out device comprising:

a main body being arrangeable on one side of the wall-like tissues in a wall-thickness direction of the wall-like tissues;

a perforating member for forming a perforation hole being perforated in the wall-like tissues in a first direction from the one side toward an other side, wherein the perforating member is movable relative to the main body; and a connector configured to connect the perforating member and the inserting member, wherein the connector comprises a first connecting portion being connectable to the perforating member at one end side of the connector and a second connecting portion being connectable to the inserting member at an other end side of the connector, wherein the perforating member has a tip portion, and a perforating shaft portion to be a part inserted into the wall-like tissues, wherein the perforating shaft portion is adjacent to the tip portion in a length direction of the perforating member, wherein a maximum dimension of the perforating shaft portion in a radial direction of the inserting member is smaller than an outer diameter of the inserting member, wherein the main body has a lead-out hole having an inner space extending along the first direction, wherein the perforating member is configured to be guided in the first direction and in a second direction opposite to the first direction in an interior of the lead-out hole coaxially to an axial center of the lead-out hole, and wherein the lead-out hole has a size allowing the connector and the inserting member to be inserted through the lead-out hole when the perforating member is moved in the second direction in a state in which the perforating member is connected to the connector with the connector being connected to the inserting member at the other side of the wall-like tissues.

2. The inserting member lead-out device according to claim 1, wherein the inserting member lead-out device further comprises a guide member being insertable at least partially into the lead-out hole, wherein the guide member has a guide hole to guide the perforating member coaxially to the axial center of the lead-out hole, and wherein the guide member is configured to be pulled out from the lead-out hole, together with the perforating member.

3. The inserting member lead-out device according to claim 2, wherein the guide member comprises a tubular guide portion to be inserted into the lead-out hole, and an extended portion provided to a side in the second direction relative to the guide portion, wherein the extended portion extends radially outward relative to an outer periphery of the guide portion, and wherein the guide member has an engaging portion to engage with the main body to suppress the guide portion of the guide member from detaching from the lead-out hole.

4. The inserting member lead-out device according to claim 1, wherein the perforating member has a stopper portion to restrict an amount of protrusion from the main body of the perforating member to be within a predetermined range.

5. The inserting member lead-out device according to claim 1, wherein the connector has a widened portion in which a width in the radial direction is widened to widen the perforation hole perforated with the perforating member when the perforating member is moved in the second direction in the state in which the perforating member is connected to the connector with the connector being connected to the inserting member at the other side of the wall-like tissues.

6. The inserting member lead-out device according to claim 5, wherein the widened portion has a tapered portion formed in a shape of a truncated cone widening toward the other end side from the one end side of the connector, and a maximum outer diameter of the tapered portion is equal to or larger than the outer diameter of the inserting member.

\* \* \* \* \*